(12) United States Patent
Marziali et al.

(10) Patent No.: US 9,534,304 B2
(45) Date of Patent: *Jan. 3, 2017

(54) SCODAPHORESIS AND METHODS AND APPARATUS FOR MOVING AND CONCENTRATING PARTICLES

(71) Applicant: The University of British Columbia, Vancouver (CA)

(72) Inventors: Andrea Marziali, North Vancouver (CA); Lorne Whitehead, Vancouver (CA)

(73) Assignee: The University of British Columbia, Vancouver (CA)

( * ) Notice: Subject to any disclaimer, the term of this patent is extended or adjusted under 35 U.S.C. 154(b) by 721 days.

This patent is subject to a terminal disclaimer.

(21) Appl. No.: 13/925,447

(22) Filed: Jun. 24, 2013

(65) Prior Publication Data
US 2013/0292249 A1 Nov. 7, 2013

Related U.S. Application Data

(63) Continuation of application No. 13/360,640, filed on Jan. 27, 2012, now Pat. No. 8,480,871, which is a
(Continued)

(51) Int. Cl.
*G01N 27/447* (2006.01)
*C25B 7/00* (2006.01)
(Continued)

(52) U.S. Cl.
CPC ............... *C25B 7/00* (2013.01); *B01D 57/02* (2013.01); *G01N 27/44713* (2013.01);
(Continued)

(58) Field of Classification Search
CPC ............ G01N 27/447; G01N 27/44734; G01N 27/44786; G01N 27/44791; G01N 27/453
See application file for complete search history.

(56) References Cited

U.S. PATENT DOCUMENTS

| 4,148,703 A | 4/1979 | Trop et al. |
| 4,390,403 A | 6/1983 | Batchelder |

(Continued)

FOREIGN PATENT DOCUMENTS

| CA | 2552262 A1 | 8/2005 |
| CA | 2523089 A1 | 4/2006 |

(Continued)

OTHER PUBLICATIONS

Asbury, et al., "Trapping of DNA by dielectrophoresis", Electrophoresis, 2002, 23:2658-2666.
(Continued)

*Primary Examiner* — Alexander Noguerola
(74) *Attorney, Agent, or Firm* — Brown Rudnick LLP

(57) ABSTRACT

Methods and apparatus for moving and concentrating particles by applying an alternating driving field and an alternating field that alters mobility of the particles. The driving field and mobility-varying field are correlated with one another. The methods and apparatus may be used to concentrate DNA or RNA in a medium, for example. Methods and apparatus for extracting particles from one medium into another involve applying an alternating driving field that causes net drift of the particles from the first medium into the second medium but no net drift of the particles in the second medium.

13 Claims, 21 Drawing Sheets

Related U.S. Application Data continuation of application No. 10/597,307, filed as application No. PCT/CA2005/000124 on Feb. 2, 2005, now Pat. No. 8,133,371.

(60) Provisional application No. 60/540,352, filed on Feb. 2, 2004, provisional application No. 60/634,604, filed on Dec. 10, 2004.

(51) Int. Cl.
*B01D 57/02* (2006.01)
*B03C 5/00* (2006.01)
*G01N 1/40* (2006.01)

(52) U.S. Cl.
CPC ........ *G01N 27/44734* (2013.01); *B03C 5/005* (2013.01); *G01N 27/44786* (2013.01); *G01N 2001/4038* (2013.01)

(56) References Cited

U.S. PATENT DOCUMENTS

| | | | |
|---|---|---|---|
| 4,390,404 A | 6/1983 | Esho et al. | |
| 4,732,656 A | 3/1988 | Hurd | |
| 4,911,817 A | 3/1990 | Kindlmann | |
| 4,971,671 A | 11/1990 | Slater et al. | |
| 5,084,157 A | 1/1992 | Clark et al. | |
| 5,185,071 A | 2/1993 | Serwer et al. | |
| 5,286,434 A | 2/1994 | Slater et al. | |
| 5,384,022 A | 1/1995 | Rajasekaran | |
| 5,453,162 A | 9/1995 | Sabanayagam et al. | |
| 5,609,743 A | 3/1997 | Sasagawa et al. | |
| 5,641,628 A | 6/1997 | Bianchi | |
| 5,938,904 A | 8/1999 | Bader et al. | |
| 6,036,831 A | 3/2000 | Bishop | |
| 6,110,670 A | 8/2000 | Van Broeckhoven et al. | |
| 6,146,511 A | 11/2000 | Slater et al. | |
| 6,193,866 B1 | 2/2001 | Bader et al. | |
| 6,258,540 B1 | 7/2001 | Lo et al. | |
| 6,693,620 B1 | 2/2004 | Herb et al. | |
| 6,824,664 B1 | 11/2004 | Austin et al. | |
| 6,827,830 B1 | 12/2004 | Slater et al. | |
| 6,893,546 B2 | 5/2005 | Jullien et al. | |
| 6,927,028 B2 | 8/2005 | Dennis et al. | |
| 7,175,747 B2 | 2/2007 | Bayerl et al. | |
| 7,198,702 B1 | 4/2007 | Washizu et al. | |
| 7,371,533 B2 | 5/2008 | Slater et al. | |
| 7,427,343 B2 | 9/2008 | Han et al. | |
| 7,442,506 B2 | 10/2008 | Dhallan | |
| 7,452,668 B2 | 11/2008 | Boles et al. | |
| 7,838,647 B2 | 11/2010 | Hahn et al. | |
| 7,888,017 B2 | 2/2011 | Quake et al. | |
| 8,008,018 B2 | 8/2011 | Quake et al. | |
| 8,133,371 B2 | 3/2012 | Marziali et al. | |
| 8,182,666 B2 | 5/2012 | Marziali et al. | |
| 8,195,415 B2 | 6/2012 | Fan et al. | |
| 8,480,871 B2 * | 7/2013 | Marziali | B01D 57/02 204/457 |
| 2001/0045359 A1 | 11/2001 | Cheng et al. | |
| 2002/0036139 A1 | 3/2002 | Becker et al. | |
| 2002/0081280 A1 | 6/2002 | Curiel et al. | |
| 2002/0119448 A1 | 8/2002 | Sorge et al. | |
| 2002/0179445 A1 | 12/2002 | Alajoki et al. | |
| 2003/0027178 A1 | 2/2003 | Vasmatzis et al. | |
| 2003/0215855 A1 | 11/2003 | Dubrow et al. | |
| 2005/0164241 A1 | 7/2005 | Hahn et al. | |
| 2005/0164402 A1 | 7/2005 | Belisle et al. | |
| 2005/0247563 A1 | 11/2005 | Shuber et al. | |
| 2005/0247564 A1 | 11/2005 | Volkel et al. | |
| 2007/0215472 A1 | 9/2007 | Slater et al. | |
| 2007/0218494 A1 | 9/2007 | Slater et al. | |
| 2008/0108063 A1 | 5/2008 | Lucero et al. | |
| 2008/0314751 A1 | 12/2008 | Bukshpan et al. | |
| 2009/0120795 A1 | 5/2009 | Marziali et al. | |
| 2009/0139867 A1* | 6/2009 | Marziali | B01D 57/02 204/549 |
| 2009/0152116 A1 | 6/2009 | Boles et al. | |
| 2010/0273219 A1 | 10/2010 | May et al. | |
| 2010/0285537 A1 | 11/2010 | Zimmermann | |
| 2011/0048950 A1 | 3/2011 | Marziali et al. | |
| 2011/0152111 A1 | 6/2011 | Fan et al. | |
| 2011/0245482 A1 | 10/2011 | Hahn et al. | |
| 2011/0272282 A1 | 11/2011 | Marziali et al. | |
| 2012/0035062 A1 | 2/2012 | Schultz et al. | |
| 2012/0048735 A1 | 3/2012 | Marziali et al. | |
| 2012/0160682 A1* | 6/2012 | Marziali | B01D 57/02 204/456 |
| 2012/0199481 A1 | 8/2012 | Marziali et al. | |

FOREIGN PATENT DOCUMENTS

| | | |
|---|---|---|
| CA | 2496294 A1 | 8/2006 |
| CA | 2641326 A1 | 8/2006 |
| CA | 2713313 A1 | 8/2009 |
| CA | 2742460 A1 | 5/2010 |
| EP | 0356187 A2 | 2/1990 |
| EP | 1720636 A1 | 11/2006 |
| EP | 1859249 | 11/2007 |
| EP | 2238434 | 10/2010 |
| EP | 2458004 A1 | 5/2012 |
| GB | 2249395 A | 5/1992 |
| JP | 7-167837 A | 7/1995 |
| JP | 2000-505545 A | 5/2000 |
| JP | 2001-165906 A | 6/2001 |
| JP | 2002-502020 A | 1/2002 |
| JP | 2003-062401 A | 3/2003 |
| JP | 2003-066004 A | 3/2003 |
| JP | 2003-513240 A | 4/2003 |
| JP | 2003-215099 A | 7/2003 |
| JP | 2003-247980 A | 9/2003 |
| WO | 9514923 A1 | 6/1995 |
| WO | 9727933 A1 | 8/1997 |
| WO | 9938874 A2 | 8/1999 |
| WO | 9945374 A2 | 9/1999 |
| WO | 2001031325 A1 | 5/2001 |
| WO | 0242500 A2 | 5/2002 |
| WO | 03019172 A2 | 3/2003 |
| WO | 2005072854 A1 | 8/2005 |
| WO | 2006063625 A1 | 6/2006 |
| WO | 2006081691 A1 | 8/2006 |
| WO | 2007092473 A2 | 8/2007 |
| WO | 2009094772 A1 | 8/2009 |
| WO | 2010051649 A1 | 5/2010 |
| WO | 2010104798 A1 | 9/2010 |
| WO | 2010121381 A1 | 10/2010 |
| WO | 201302616 A2 | 1/2013 |

OTHER PUBLICATIONS

Asbury, et al., "Trapping of DNA in Nonuniform Oscillating Electric Fields", Biophysical Journal, 1998, 74:1024-1030.
Astumian, et al., "Fluctuation Driven Ratchets: Molecular Motors", Physical Review Letters, 1994, 72(11):1766-1769.
Baba, Yoshinobu, "Capillary Affinity Gel Electrophoresis", Molecular Biotechnology, 1996, (9):1-11.
Bier, Martin, et al., "Biasing Brownian Motion in Different Directions in a 3-State Fluctuating Potential and an Application for the Separation of Small Particles", Physical Review Letters, 1996, 76(22):4277-4280.
Broemeling, D., et al., "An Instrument for Automated Purification of Nucleic Acids from Contaminated Forensic Samples", JALA 2008, 13, 40-48.
Carle, G.F., et al., "Electrophoretic Separations of Large DNA Molecules by Periodic Inversion of the Electric Field", Science, 1986, 232(4726):65-68.
Chacron, M.J., et al., "Particle trapping and self-focusing in temporarily asymmetric ratchets with strong field gradients", Physical Review E, 1997, 56(3):3446-3450.
Chakrabarti, Subrata, et al., "Highly Selective Isolation of Unknown Mutations in Diverse DNA Fragments: Toward New Multiplex

(56) References Cited

OTHER PUBLICATIONS

Screening in Cancer", American Association for Cancer Reserch, 2000, 60:3732-3737.
Chan, K.C. Allen, et al., "Size Distributions of Maternal and Fetal DNA in Maternal Plasma", Molecular Diagnostics and Genetics, Clinical Chemistry, 2004, 50(1):88-92.
Chu, Gilbert, "Bag model for DNA migration during pulsed-field electrophoresis", Proc. Natl. Acad. Sci., 1991, 88:11071-11075.
European Search Report corresponding to EP11004417, Mar. 29, 2012, 4 pages.
Frumin, L.L., et al., "Anomalous size dependence of the non-linear mobility of DNA", In PhysChemComm, 2000, 11 (3):61-63.
Frumin, L.L., et al., "Nonlinear focusing of DNA macromolecules", Physical Review E—Statistical, Nonlinear and Soft Matter Physics, 2001, 64:021902-1-5.
Griess, Gary A., et al., "Cyclic capillary electrophoresis", Electrophoresis, 2002, 23:2610-2617.
International Preliminary Report on Patentability corresponding to PCT/CA2005/000124, Aug. 7, 2006, 8 pages.
International Preliminary Report on Patentability corresponding to PCT/CA2006/000172, Aug. 7, 2007, 8 pages.
International Preliminary Report on Patentability corresponding to PCT/CA2009/000111, Aug. 3, 2010, 9 pages.
International Seach Report and Written Opinion for PCT/US13/39553 dated Sep. 18, 2013, pp. 13.
International Search Report dated Feb. 23, 2010 corresponding to PCT/CA2009/001648, 6 pages.
International Search Report for PCT/CA2006/000172, International Searching Authority, Jun. 2, 2006, 4 pages.
International Search Report for PCT/CA2012/050576, Feb. 28, 2013 3 pages.
Jorgez, Carolina J., et al., "Quantity versus quality: Optimal methods for cell-free DNA isolation from plasma of pregnant women", American College of Medical Genetics, 2006, 8(10):615-619.
Kitzman, Jacob O., et al., "Noninvasive Whole-Genome Sequencing of a Human Fetus", Sci Transl Med 4, 137ra76 (2012); DOI: 10.1126/scitranslmed.3004323, 9 pages.
Kopecka, K., et al., "Capillary electrophoresis sequencing of small ssDNA molecules versus the Ogston regime: Fitting data and interpreting parameters", Electrophoresis, 2004, 25(14):2177-2185.
LaLande, Marc, et al., "Pulsed-field electrophoresis: Application of a computer model to the separation of large DNA molecules", Proc. Natl. Acad. Sci. USA, 1987, 84:8011-8015.
Lun, Fiona M. F., et al., "Microfluidics Digital PCR Reveals a Higher than Expected Fraction of Fetal DNA in Maternal Plasma", Molecular Diagnostics and Genetics, Clinical Chemistry, 2008, 54(10):1664-1672.
Magnasco, Marcelo O., "Forced Thermal Ratchets", Physical Review Letters, 1993, 71(10):1477-1481.
Makridakis, Nick M., "PCR-free method detects high frequency of genomic instability in prostate cancer", Nucleic Acids Research, 2009, 37(22):7441-7446.

Marziali, A., et al., "Novel electrophoresis mechanism based on synchronous alternating drag perturbation", Electrophoresis 2005, 26:82-90, published on-line Dec. 29, 2004 at URL www.3.interscience.wiley.com/cgi-bin/issue/109861245.
Nollau, Peter, et al., "Methods for detection of point mutations: performance and quality assessment", Department of Clinical Chemistry, 1997, 43(7):1114-1128.
Office Action mailed Aug. 19, 2011 for U.S. Appl. No. 11/815,760.
Office Action mailed Dec. 27, 2010 for U.S. Appl. No. 11/815,760.
Pel, J., "A novel electrophoretic mechanism and separation parameter for selective nucleic acid concentration based on synchronous coefficient of drag alteration (SCODA)", (Ph.D. Thesis), Vancouver: University of British Columbia, 2009.
Pel, J., et al., "Nonlinear electrophoretic response yields a unique parameter for separation of biomolecules", PNAS 2009, vol. 106, No. 35, 14796-14801.
Rousseau, J., et al., "Gel electrophoretic mobility of single-stranded DNA: The two reptation field-dependent factors", Electrophoresis, 2000, 21(8):1464-1470.
Sikora, Aleksandra, et al., "Detection of Increased Amounts of Cell-Free DNA with Short PCR Amplicons", Clinical Chemistry, 2010, 56(1):136-138.
Slater, G.W., et al., "Recent developments in DNA electrophoretic separations", Electrophoresis, 1998, 19(10):1525-1541.
Slater, G.W., et al., "The theory of DNA separation by capillary electrophoresis", Current Opinion in Biotechnology, 2003, 14:58-64.
Slater, G.W., et al., "Theory of DNA electrophoresis: A look at some current challenges", Electrophoresis, 2000, 21:3873-3887.
So. A., et al., "Efficient genomic DNA extraction from low target concentration bacterial cultures using SCODA DNA extraction technology", Cold Spring Harb Protoc, 2010, 1150-1153; 1185-1198.
Supplementary European Search Report corresponding to EP09706657, May 12, 2011, 2 pages.
Supplementary Partial European Search Report corresponding to EP05706448, May 14, 2012, 3 pages.
Tessier, F. et al., "Strategies for the separation of polyelectrolytes based on non-linear dynamics and entropic ratchets in a simple microfluidic device", Applied Physics A—Materials Science & Processing, 2002, 75:285-291.
Turmel, C., et al., "Molecular detrapping and band narrowing with high frequency modulation of pulsed field electrophoresis", Nucleic Acids Research, 1990, 18(3):569-575.
Viovy, J.L., "Electrophoresis of DNA and other polyelectrolytes: Physical mechanisms", Review of Modern Physics, 2000, 72(3):813-872.
Wright, Caroline, "Cell-free fetal nucleic acids for non-invasive prenatal diagnosis", Report of the UK export working group, Jan. 2009, 64 pages.
Yobas, L., et al., "Nucleic Acid Extraction, Amplification, and Detection on Si-Based Microfluidic Platforms," IEEE Journal of Solid-State Circuits, vol. 42, No. 8, Aug. 2007, 12 pages.

* cited by examiner

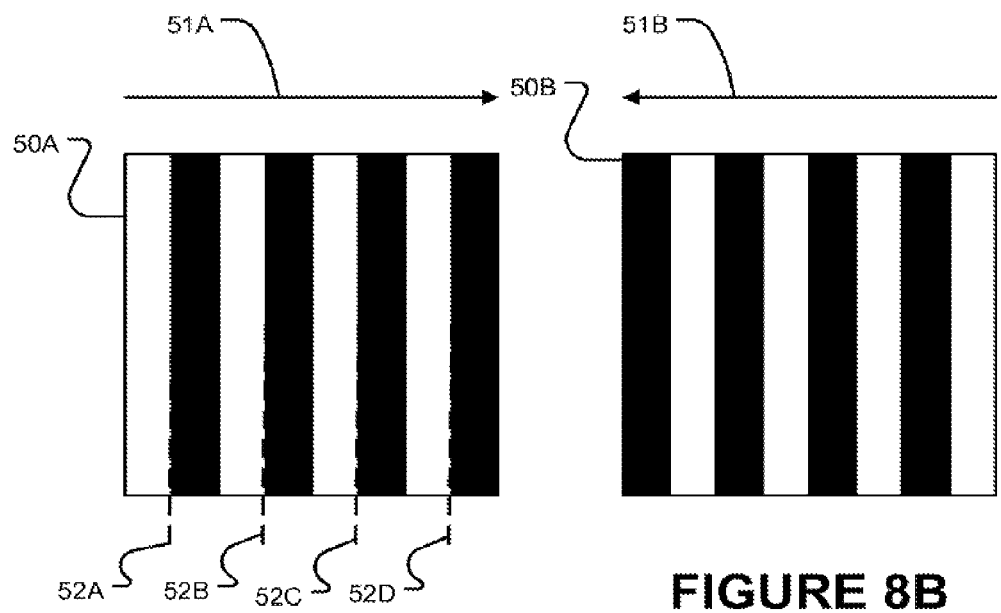
FIGURE 8A
FIGURE 8B
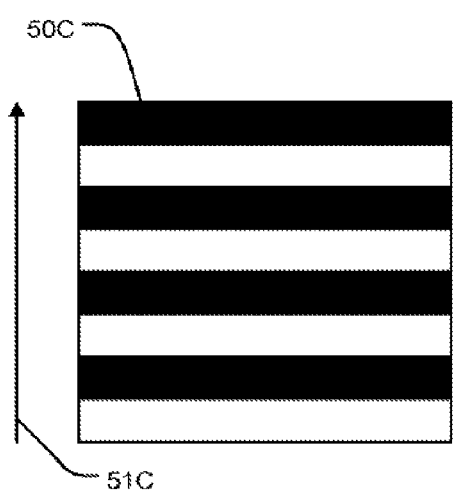
FIGURE 8C
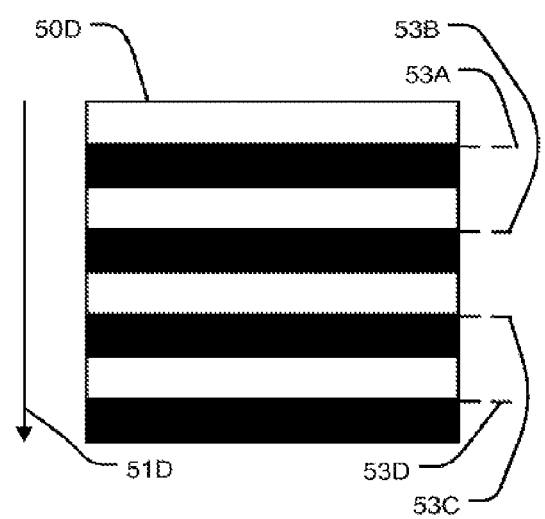
FIGURE 8D

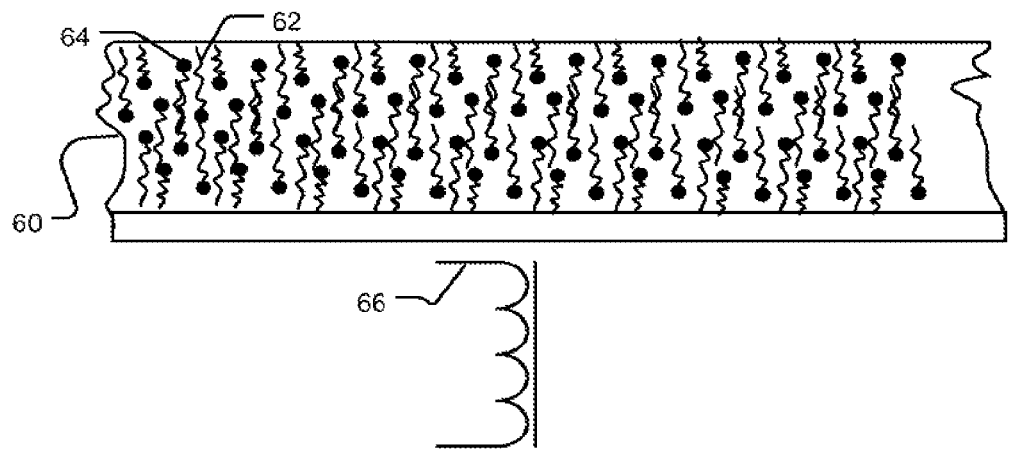
FIGURE 10A
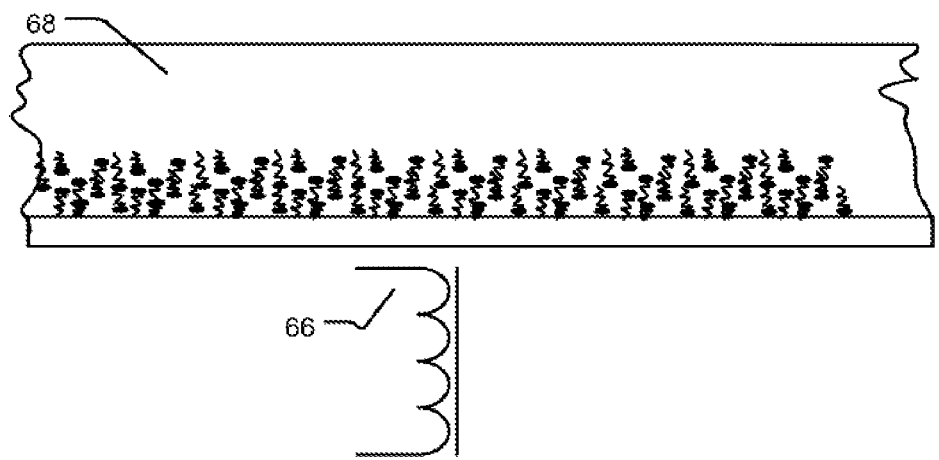
FIGURE 10B
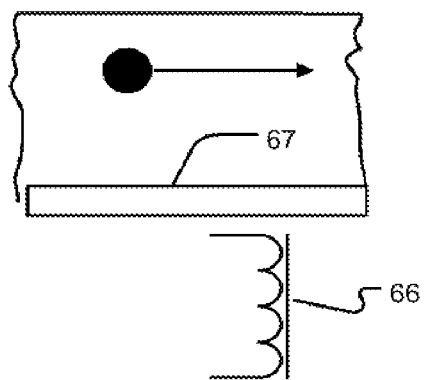 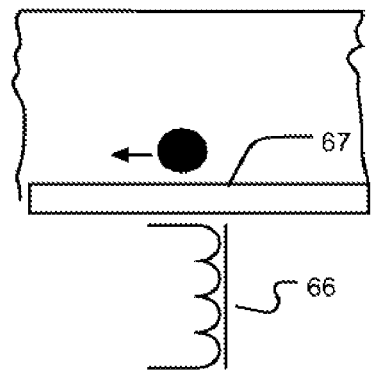
FIGURE 10C      FIGURE 10D

SCODAPHORESIS AND METHODS AND APPARATUS FOR MOVING AND CONCENTRATING PARTICLES

CROSS-REFERENCE TO RELATED APPLICATIONS

This application is a continuation of U.S. application Ser. No. 13/360,640, filed Jan. 27, 2012 which is a continuation of U.S. application Ser. No. 10/597,307, which is a 371 of International Application No. PCT/CA2005/000124 filed on 2 Feb. 2005, which claims the benefit of the filing date of U.S. application No. 60/540,352 filed on 2 Feb. 2004 and U.S. application No. 60/634,604 filed on 10 Dec. 2004, which are all hereby incorporated herein by reference.

TECHNICAL FIELD

The invention relates to methods and apparatus for moving and concentrating particles. The invention has application, for example, in moving and/or concentrating particles of a wide range of types. Some examples of particles that can be moved and/or concentrated by embodiments of the invention include molecules such as nucleic acids, proteins, other bio-macromolecules, inorganic or inorganic ions, and other particles of molecular size and larger including suitable magnetic particles, and other particles.

BACKGROUND

Pathogens and certain diseases can be identified in the environment or in a patient by detecting DNA associated with the pathogen or disease in environmental samples, body fluids, water, or other contaminated solutions. DNA can also be extracted from crime scenes and associated evidence. It is generally necessary to concentrate DNA before the DNA can be identified. DNA can be concentrated by filtration. However, filtration technologies are inefficient. Filters fine enough to trap DNA, viruses or the like are easily clogged with other debris. There is a general need for technologies capable of concentrating DNA and similar materials and/or extracting relatively pure DNA from contaminated solutions.

Laborious and/or expensive purification methods are often employed to prepare samples containing nucleic acids for biochemical assays. The polymerase chain reaction (PCR) can be used to amplify the concentrations of nucleic acids such as DNA and RNA. However, PCR can be undesirably expensive, especially for large volume samples.

Electrophoresis involves directing the movement of charged particles in a medium, such as a gel or liquid solution by applying an electric field across the medium. The electric field may be generated by applying a potential across electrodes that are placed in contact with the medium such that electric current can be conducted into the medium. The movement of the particles in the medium is affected by the magnitude and direction of the electric field, the electrophoretic mobility of the particles and the mechanical properties, such as viscosity, of the medium. Through electrophoresis, particles that are distributed in a medium can be transported through the medium. Electrophoresis is commonly used to transport nucleic acids (such as DNA or RNA) through gel substrates. Since different species have different electrophoretic mobilities, electrophoresis may be used to separate different species from one another. Conventional electrophoresis techniques are largely limited in application to the linear separation of charged particles.

Using conventional electrophoresis techniques, a direct current (DC) electric field or an alternating pulsed-field electrophoretic (PFGE) field is typically applied to a medium so that particles in the medium are transported toward an electrode.

Electrophoresis may be used to transport fragments of DNA or other microscopic electrically charged particles. Various electrophoresis methods are described in Slater, G. W. et al. *Electrophoresis* 2000, 21, 3873-3887. Electrophoretic particle transport is typically performed in one dimension by applying a direct current (DC) electric field between electrodes on either side of a suitable electrophoresis gel. The electric field causes electrically charged particles in the gel to move toward one of the electrodes. Electrophoresis is typically used to separate particles of different types from one another.

Electrophoresis can also be used to concentrate particles in a particular location. A problem that can interfere with the successful use of electrophoresis for concentrating particles in some applications is that there must be an electrode at the location where the particles are to be concentrated. Electrochemical interactions between the electrodes and particles can degrade certain kinds of the particles. For example, where the particles comprise DNA, the DNA can be damaged by electrochemical interactions at the electrodes.

Electric fields present during conventional direct current electrophoresis are divergence-free everywhere except at electrodes which can source or sink electric current. Electrophoresis is typically applied in cases where particles are caused to move toward an electrode.

An asymmetric alternating current (AC) waveform can cause net drift of electrophoretic particles due to nonlinearity of the relationship between particle speed and applied electric field. This effect can be used to cause particles to move in one dimension as described in Chacron, M. J., et al. Phys. Rev. E 1997, 56, 3446-3450; Frumin, L. L, et al. Phys. Chem. Commun. 2000, 11; and, Frumin, L. L. et al. Phys. Rev. E 2001, 64, 021902.

Pohl, H. A., *Dielectrophoresis: The Behavior of Neutral Matter in Nonuniform Electric Fields* Cambridge University Press, Cambridge, UK 1978; Asbury, C. L., et al., *Electrophoresis* 2002, 23, 2658-2666; and Asbury, C. L., et al. Biophys. J. 1998, 74, 1024-1030 disclose that dielectrophoresis can be applied to concentrate DNA in two or more dimensions. However, practical applications of dielectrophoresis require undesirably high electric field gradients.

One can isolate particles which have been separated from other particles by electrophoresis by cutting out the portion of the medium in which the particles have been carried by electrophoresis. The particles can be separated from the medium by using various purification techniques.

References which describe methods for DNA separation include: Slater et al. *The theory of DNA separation by capillary electrophoresis* Current Opinion in biotechnology 2003 14:58-64; Slater et al. U.S. Pat. No. 6,146,511 issued 14 Nov. 2000; Frunin et al. *Nonlinear focusing of DNA macromolecules* Phys. Rev. E 64:021902; Griess et al. *Cyclic capillary electrophoresis* Electrophoresis 2002, 23,2610-2617 Wiley-VCH Verlag GmbH & Co. Weinheim (2002). References which describe the use of fields to separate particles include: Bader et al. U.S. Pat. No. 5,938,904 issued on Aug. 17, 1999; Bader et al. U.S. Pat. No. 6,193,866 issued on 27 Feb., 2001; Tessier et al: *Strategies for the separation of polyelectrolytes based on non-linear dynamics and entropic ratchets in a simple microfluidic device* Appl. Phys. A 75, 285-291 (2002); Chacron et al. *Particle trapping and self-focusing in temporally asymmet-*

*ric ratchets with strong field gradients* Phys. Rev. B 56:3 3446-3550 (September 1997); Dean et al. *Fluctuation driven ratchets: molecular motors* Phys. Rev. Lett. 72:11 1766-1769 (14 Mar. 1994); Bier et al. *Biasing Brownian motion in different directions in a 3-state fluctuating potential and an application for the separation of small particles* Phys. Rev. Lett. 76:22 4277-4280 (27 May 1996); Magnasco, *forced thermal ratchets* Phys. Rev. Lett. 71:10 1477-1481 (6 Sep. 1993).

There remains a need for methods for moving and/or concentrating particles that improve on prior art methods and avoid limitations of prior art methods in specific applications. There also remains a need for effective methods for extracting materials such as DNA from media such as gels.

SUMMARY OF THE INVENTION

One aspect of the invention provides methods for causing motion of particles in a medium. The methods may be used for concentrating particles and/or for separating particles of different types from one another. Such methods comprise applying a time-varying driving field to the particles. The driving field applies a time-varying driving force alternating in direction to the particles. The methods also comprise applying a mobility-varying field to the particles. The mobility-varying field is one or both of: different in type from the driving field, and non-aligned with the driving field. The driving field and mobility-varying field are applied simultaneously during a period and the mobility-varying field causes a mobility of the particles in the medium to be time dependent during the period, in a manner having a non-zero correlation with the driving field over the period. These methods may be called SCODA methods.

Another aspect of the invention provides methods and apparatus for extracting charged particles from a medium. These methods may be applied to extracting particles from a medium which have been concentrated by SCODA and may also be applied to extracting from a medium particles which have not been concentrated by SCODA. A buffer in an extraction reservoir is placed to abut a medium containing the particles to be extracted at a buffer-gel interface. Electrodes are provided on each side of the buffer-gel interface. By applying a pulsed voltage potential to the electrodes (wherein the time-averaged electric field is zero), zero-integrated-field electrophoresis (ZIFE) is applied to the buffer-gel interface to direct the particles in the gel into the extraction reservoir, where the particles are collected and concentrated.

A method according to one aspect of the invention comprises placing a buffer extraction reservoir next to a gel solution containing the charged particles to be extracted; applying ZIFE to the buffer-gel interface to direct the particles into the extraction reservoir; and collecting and concentrating the particles in the extraction reservoir. A pipette or other device may then be used to suction the particles from the extraction reservoir.

In some embodiments of the invention, the apparatus comprises a gel boat holding a gel that contains the charged particles to be extracted. A capillary containing a small amount of buffer is inserted into the gel solution. A pipette or other device is provided in the capillary for suctioning the particles that have collected in the buffer. Electrodes are provided on each side of the buffer-gel interface for generating an electric field.

Further aspects of the invention and features of specific embodiments of the invention are described below.

BRIEF DESCRIPTION OF THE DRAWINGS

In drawings which illustrate non-limiting embodiments of the invention,

FIGS. 8A, 8B, 8C and 8D show optical mask patterns that may be used to cause concentration of particles at an array of spots;

FIGS. 10A, 10B, 10C and 10D show schematically apparatus for using magnetic fields to alter the mobility of particles;

DESCRIPTION

Figure 1A:
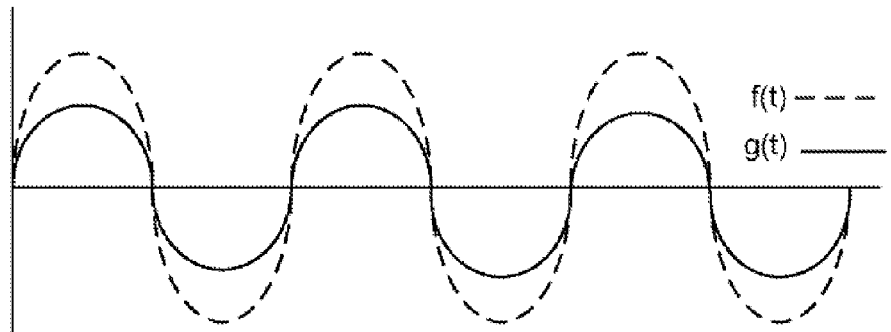
FIGS. 1A through 1I are examples of possible waveforms for driving and mobility-modifying fields.

Throughout the following description, specific details are set forth in order to provide a more thorough understanding of the invention. However, the invention may be practised without these particulars. In other instances, well known elements have not been shown or described in detail to avoid unnecessarily obscuring the invention. Accordingly, the specification and drawings are to be regarded in an illustrative, rather than a restrictive, sense.

Scodaphoresis (which is referred to herein by the coined acronym SCODA) describes methods for moving and/or concentrating particles in a medium. SCODA is an acronym for synchronous coefficient of drag alteration. "phoresis" is a combining form meaning to carry or transmit. Scodaphoresis involves exposing particles that are to be moved and/or concentrated to two time-varying fields or stimuli. A first one of the fields results in a force f(t) that drives motion of the particles in the medium. The direction of particle motion caused by the interaction of the particle with the first field varies in time. The first field may provide a driving force that averages to zero over an integral number of cycles of the first field.

A second one of the fields alters the mobility of the particles in the medium according to a function g(t). The first and second fields are such that f(t) and g(t) have a non-zero correlation over a time period of interest. Achieving such a non-zero correlation can be achieved in various ways. In some embodiments, f(t) and g(t) are each time varying at the same frequency and f(t) and g(t) are synchronized so that there is a substantially constant phase relationship between f(t) and g(t). In other embodiments, f(t) has a frequency that is twice that of g(t).

Application of the fields to the particles causes a net drift of the particles. This net drift can be harnessed to separate particles of different types or to concentrate particles in selected areas, or both. As discussed below, the first and second fields may be of the same type (homogeneous SCODA) or of different types (heterogeneous SCODA).

As a demonstration of SCODA, consider the case where:

$$f(t)=\sin(\omega t),\ g(t)=\sin(\omega t),\ \text{and}\ v(f(t),g(t))=f(t)\times(\mu_0+\mu_1 g(t)) \quad (1)$$

where $\mu_0$ is the unperturbed mobility of the particle in the medium and $\mu_1$ is the susceptibility of the mobility to g(t). It can be seen that in the absence of g(t), the velocity of the particle is given simply by $\mu_0$ f(t). Where f(t) is given by Equation (1) there is no net displacement of the particle over a cycle of f(t). Where g(t) is as given above, however, over one cycle, the velocity integrates to yield a distance, d, travelled by the particle of:

$$d = \int_{t=0}^{2\pi/\omega} \mu_1 \sin^2(\omega t)\, dt = \frac{\mu_1 \pi}{\omega} \quad (2)$$

Thus, the simultaneous application of the two fields imparts a net motion to the particle. In this example, the net motion is independent of $\mu_0$.

"Particle" is used herein to mean any microscopic or macroscopic thing that can be moved by scodaphoresis.

The correlation of f(t) and g(t) may be computed according to a suitable correlation function such as:

$$C_{f(t),g(t)} = \int_T f(t) g(t+\lambda)\, dt \quad (3)$$

where C is the correlation, T is a period of interest, and $\lambda$ is a constant time shift. C must have a non-zero value for some value of $\lambda$.

Ideally f(t) and g(t) have a large correlation for efficient operation of SCODA, but some SCODA motion can occur even in cases where the chosen functions f(t) and g(t) and the chosen value of $\lambda$ result in small values of C. The velocity of the particle undergoing SCODA motion must be a function of both f(t) and g(t). Further, the velocity of the particle as a result of the application of f(t) and g(t) together must not be the same as the sum of the velocities resulting from application of f(t) and g(t) independently. That is:

$$\vec{v}(f(t),g(t)) \neq \vec{v}(f(t),0) + \vec{v}(0,g(t+\lambda)) \quad (4)$$

One set of conditions which is convenient, but not necessary, for scodaphresis is:

$$\int_{-\infty}^{\infty} f(t)\,dt = 0, \int_{-\infty}^{\infty} g(t)\,dt = 0,\ \int_{-\infty}^{\infty} v(f(t),0)\,dt = 0,\ \text{and}$$
$$\int_{-\infty}^{\infty} v(0,g(t))\,dt = 0 \quad (5)$$

where v(f(t),0) is the velocity of a particle as a function of time when the particle is interacting only with the driving field f(t); v(0,g(t)) is the velocity of a particle as a function of time when the particle is interacting only with the mobility-varying field g(t); and, $$\int_{-\infty}^{\infty} v(f(t),g(t))\,dt \neq 0 \quad (6)$$

in this case, the two fields, acting independently, do not produce any net motion of the particle. However, the combined effect of the first and second fields does result in the particle being moved with a net velocity.

To optimize SCODA one can select functions f(t) and g(t) so that the first order velocity of the particles caused by either f(t) or g(t) is zero (so particles have no net drift), and so that the combination of f(t) and g(t) acts on the particles to provide a maximum velocity. One can select f(t) and g(t) and a phase shift $\lambda$ to maximize the integral:

$$\int_0^T \vec{v}(f(t),g(t+\lambda))\,dt \quad (7)$$

The process in this case runs from time 0 to time T or possibly for multiple periods wherein t rund from 0 to T in each period.

It is not necessary that f(t) and g(t) be represented by sinusoidal functions, by the same functions, or even by periodic functions. In some embodiments of the invention, f(t) and g(t) are different functions. In some embodiments of the invention, f(t) and g(t) are not periodic. FIGS. 1A through 1H show some examples of functions f(t) and g(t) that could be used in specific embodiments of the invention.

Figure 1B:
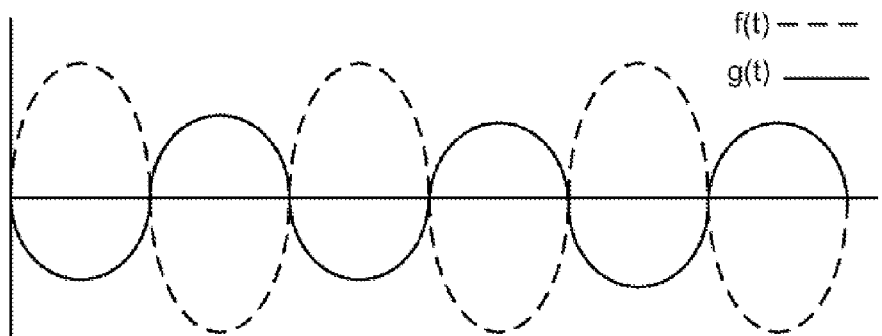

FIG. 1A shows a case wherein f(t) and g(t) are both sine functions with f(t) and g(t) in phase. FIG. 1B shows a case where f(t) and g(t) are both sine functions with f(t) and g(t) out of phase. As described below, the direction in which particles are caused to move can be reversed by altering the relative phase of f(t) and g(t).

Figure 1C:
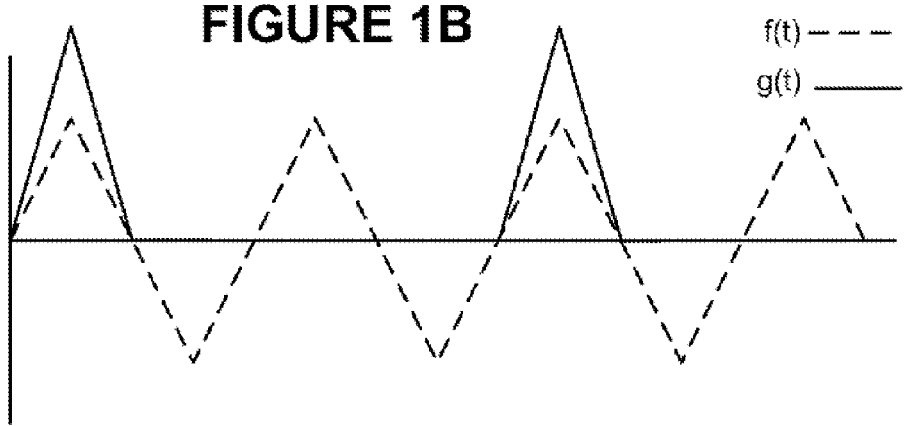
Figure 1D:
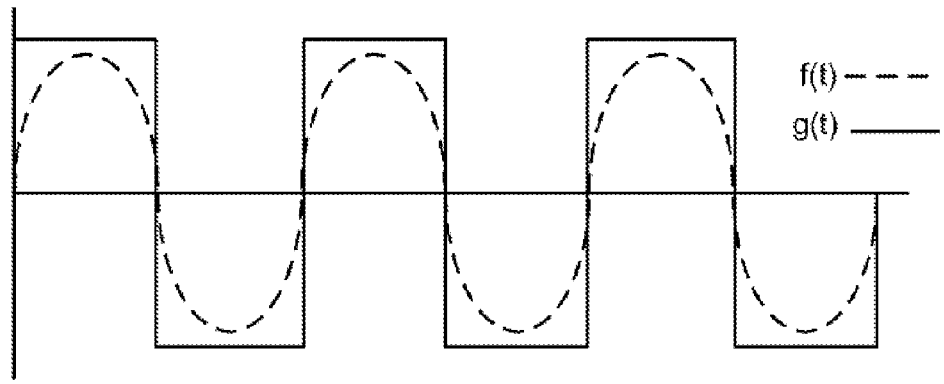
Figure 1E:
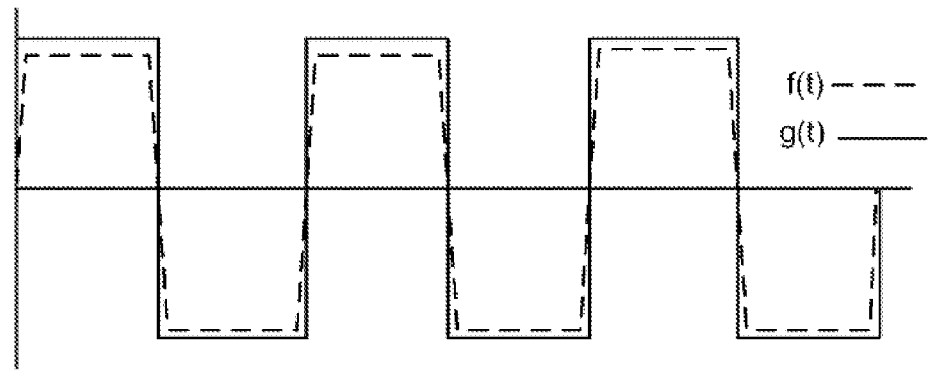
Figure 1F:
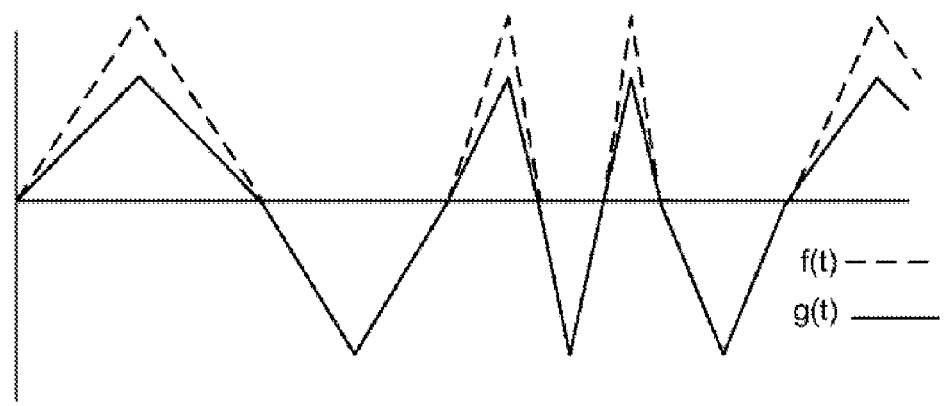
Figure 1G:
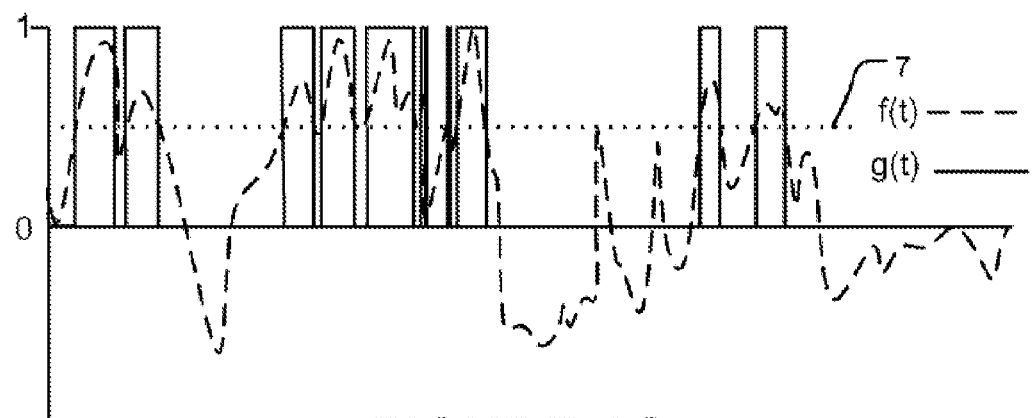
Figure 1H:
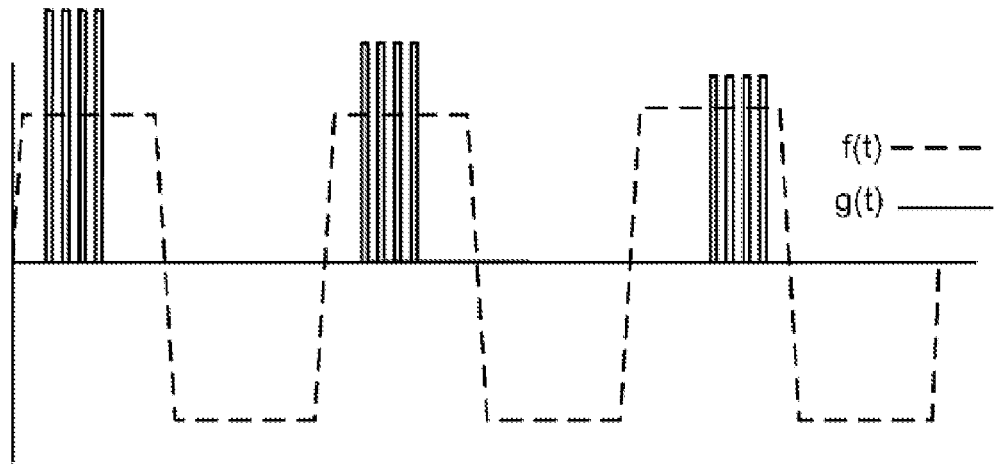

FIG. 1C shows a case where g(t) is unbalanced. In FIG. 1C, f(t) and g(t) are both triangular functions. In FIG. 1C g(t) has a frequency half of that of f(t). In FIG. 1D, f(t) has a square waveform while g(t) has a sinusoidal waveform. In FIG. 1E, f(t) and g(t) both have substantially square waveforms. In FIG. 1F, f(t) and g(t) have varying frequencies. In FIG. 1G, f(t) is essentially random noise and g(t) has a value of 1 (in arbitrary units) when f(t) exceeds a threshold 7 and has a value of 0 otherwise. In FIG. 1H, g(t) has the form of a series of short-duration impulses.

As another example, $f(t) = \sin(\omega t)$, $g(t) = 1$ for $$\frac{2n\pi}{\omega} < t < \frac{(2n+1)\pi}{\omega}$$

where n is any integer or set of integers (e.g. $n \in \{1, 2, 3, \ldots\}$ or $n \in \{2, 4, 6, \ldots\}$ or $n \in \{1, 4, 7, \ldots\}$). The integers n do not need to be regularly spaced apart. For example, the methods of the invention could be made to work in a case wherein the set of integers n consists of a non-periodic series. An otherwise periodic waveform f(t) or g(t) could be made aperiodic by randomly omitting troughs (or peaks) of the waveform, for example.

Figure 1I:
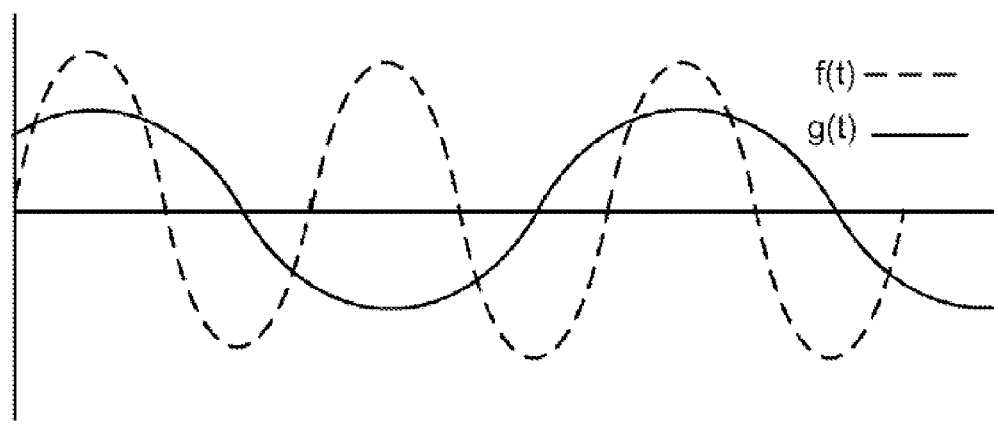

FIG. 1I illustrates a case where f(t) has a frequency twice that of g(t). The waveforms of FIG. 1I can produce SCODA motion, for example, where the mobility of particles varies in response to |g(t)|. It can be seen that |g(t)| has larger values for positive-going peaks of f(t) than for negative-going peaks of f(t).

While the waveforms shown in most of FIGS. 1A to 1I are symmetrical (i.e. they have the same overall form if inverted in spatial direction) this is not mandatory. f(t) could, in general, be asymmetrical.

Driving Fields f(t) is referred to herein as a driving function because it drives motion of the particles in the medium. In different embodiments of the invention, f(t) is produced by fields of different types. For example, f(t) may be produced by any of:
  a time-varying electric field;
  a time-varying magnetic field;
  a time-varying flow in the medium;
  a time-varying density gradient of some species in the medium;
  a time-varying gravitational or acceleration field (which may be obtained, for example by accelerating a medium containing particles and periodically changing an orientation of the medium relative to the direction of the gravitational or acceleration field);
  or the like.

In some embodiments, f(t) applies a force to particles that alternates in direction wherein the magnitude of the force is the same in each direction. In other embodiments, f(t) combines a component that alternates in direction and a bias component that does not alternate in direction such that the magnitude of the force applied to particles is larger in one direction than in the other. The bias component may be termed a DC component while the alternating component may be termed an AC component.

The driving field is selected to interact with the particles of interest. For example:
  Where the particles are electrically charged particles (ions for example), an electric field may be used for the driving field. Electrically neutral particles may be made responsive to an electric field by binding charged particles to the electrically neutral particles. In some cases an electrically neutral particle, such as a neutral molecule, can be carried by a charged particle, such as a charged molecule, For example, neutral proteins that interact with charged micelles may be driven by an electrical driving field through the interaction with the driving field and the micelles.
  Where the particles have dielectric constants different from that of the medium then an electric field having a time-varying gradient can drive motion of the particles through the medium by dielectrophoresis.
  Where the particles contain magnetic material (for example, where particles of interest can be caused to bind to small beads of a type affected by magnetic forces, for example ferromagnetic beads) a magnetic field may be used for the driving field.
  Where the particles have magnetic susceptibilities different from that of the medium then a gradient in a magnetic field may be used to drive motion of the particles relative to the medium by magnetophoresis.
  Where the particles have densities different from that of the medium then a gravitational or other acceleration acting on the particles may drive motion of the particles relative to the medium. An AC acceleration is provided in some embodiments by exposing the medium to an acoustic field.

The driving field may directly apply a force to the particles or may indirectly cause motion of the particles. As an example of the latter, the driving field may cause living particles (mobile bacteria for example) to move in response to their own preference for certain environments. For example, some organisms will swim toward light, chemical gradients, or magnetic fields (these phenomena are known as chemotaxis, phototaxis, and magnetotaxis respectively).

Mobility-Varying Fields

The mobility of particles may by altered according to any of a wide variety of mechanisms. For example:
  changing a temperature of the medium;
  exposing the particles to light or other radiation having an intensity and/or polarization and/or wavelength that varies in time with the driving field;
  applying an electric field to the portion of the medium through which the particles are passing;
  applying a magnetic field to the medium through which the particles are passing (the magnetic field may, for example, alter an orientation of a magnetic dipole associated with the particle and thereby affect a coefficient of drag of the particle or alter a viscosity of the medium which may comprise a suitable magneto-rheological fluid);
  applying an acoustic signal to the portion of the medium through which the particles are passing;
  causing a cyclic change in concentration of a species in the medium;
  exploiting electroosmotic effects;
  causing cyclic chemical changes in the medium;
  causing the particles to cyclically bind and unbind to other particles in or components of the medium;
  varying a hydrostatic pressure experienced by the medium;
  varying physical dimensions of the medium to cause a change in an effective drag experienced by particles in the medium;
  applying magnetic fields to the medium.

Any effect that varies the mobility of a particle in response to a driving field, such as an electrophoretic driving field, can be used.

In some embodiments of the invention, the mobility of particles is varied by exploiting non-linearities in the relationship between the velocity of a particle and the intensity of the driving field. Some embodiments apply a second driving field having a component acting perpendicular to the direction of the first driving field but a frequency half that of the first driving field. Applied by itself, such a second driving field would simply cause particles to oscillate back and forth in a direction perpendicular to the direction of the main driving field. When applied together with the main driving field, however, such a second driving field can cause particles to have higher average speeds relative to the medium for one direction of the main driving field than for the other direction of the main driving field. This results in a net drift of the particles because of the non-linear relationship between particle mobility and particle speed. In some embodiments the main driving field has a symmetrical waveform, such as a sinusoidal, triangular or square waveform.

A temperature of the medium in which the particles are situated may be altered in time with the driving field. The changing temperature may result in a change in one or more of a conformation of the particles, a viscosity of the medium, a strength of interaction between the particles and the medium, some combination of these, or the like. The result is that the mobility of the particles is altered by the change in temperature. The temperature of regions in a medium may be controlled in any suitable manner including:

directing radiation at the portion of the medium to heat that portion of the medium;
energizing heaters or coolers in thermal contact with the portion of the medium;
causing endothermic or exothermic chemical reactions to occur in the portion of the medium (or in a location that is in thermal contact with the portion of the medium); and,
the like.

In some embodiments of the invention the medium comprises a material that absorbs radiation and releases the absorbed radiation energy as heat. In some embodiment, localized heating of the medium in the vicinity of the particles being moved is achieved by irradiating the particles with electromagnetic radiation having a wavelength that is absorbed by the particles themselves and released as heat. In such embodiments it can be advantageous to select a wavelength for the radiation that is not absorbed or converted to heat significantly by constituents of the medium so that heating is local to the particles.

Some examples of particles that have mobilities that vary with temperature are: proteins that can be cyclically denatured or caused to fold in different ways by cyclically changing the temperature; and DNA that can be cyclically denatured.

Exposing the area of the medium in which the particles are travelling to radiation changes one or more of: a conformation of the particles, a viscosity of the medium, a strength of interaction between the particles and the medium, some combination of these, or the like. The result is that the mobility of the particles is altered by changes in the intensity and/or polarization and/or wavelength of the applied radiation. Some examples of particles that have mobilities that can be caused to change by applying light are molecules such as azobenzene or spiro-pyrans, that can be caused to undergo reversible changes in conformation by applying light. Another example of the use of light to vary the mobilities of particles in a medium is the application of light to cause partial cross-linking of polymers in a medium containing polymers.

The intensity of an electric field applied to the medium may be varied in time with the driving field. In some media the mobility of particles of certain types varies with the applied electric field. In some media the particle velocity varies non-linearly with the applied electric field.

The mobility of particles in a medium may vary with the intensity of an acoustic field applied to the medium. In some cases, an acoustic standing waves in a solution or other medium may cause transient differences in local properties of the medium (e.g. electrical resistivity) experienced by particles in the medium thus leading to local inhomogeneity in the driving field (e.g. a driving electric field).

Where mobility of particles is controlled by altering a concentration of a species, the species having the varying concentration may, for example, be a species that binds to the particles or a species that affects binding of the particles to some other species or to a surface or other adjacent structure. The species may directly affect a viscosity of the medium.

As an example of the use of electroosmotic effects to control particle mobility, consider the case where the medium in which the particles are moving is a solution containing one or more polymers. In such solutions, an applied electric field can cause bulk fluid flow. Such a flow could be controlled to provide a perturbing stimulus to a pressure or flow induced driving force, or as a perturbation to an electrical driving force, possibly exploiting non-linearities in the onset of electroosmotic flow.

Chemical changes that are exploited to control particle mobility may, for example, induce changes in one or more of:

a conformation of the particles;
a conformation of some other species;
binding of the particles to one another or to other species or structures in the medium;
binding of species in the medium to one another; viscosity of the medium; or
the like.

The chemical changes may be induced optically, for example, by optically inducing cross-linking or by optically inducing oxidation or reduction of photoactive molecules such as ferrocene. The chemical changes may be induced by introducing chemical species into the medium. The chemical changes may include one or more of changes: that alter the pH of the medium; changes that result in changes in the concentration of one or more chemical species in the medium; or the like.

Particle mobility may be affected by applied magnetic fields according to any of a variety of mechanisms. For example:

The medium may contain small magnetic beads. The beads may be linked to polymers in a polymer matrix. By applying a magnetic field, the beads may be pulled away from a path of the particles, thereby reducing an effective viscosity of the medium experienced by the particles.
The medium could be a magneto-rheological fluid having a viscosity that varies with applied magnetic field.
A magnetic field may be used to cause medium viscosity to vary according to a two-dimensional pattern. The magnetic field could change in time in such a manner that the viscosity of the medium varies with position and varies in time in a manner that provides a synchronous perturbation to a periodic driving force. As another example, where the particles themselves are magnetic, transport and concentration of the particles could be affected by a magnetic field. The particles could be driven electrophoretically. The magnetic field could be switched on periodically to drive the particles toward a drag-inducing surface, or release them from such a surface. The magnetic field could also be used to make the particles aggregate.

Particles

The methods of the invention may be applied to particles of virtually any kind including molecules, ions, and larger particulates. Some non-limiting examples of particles which may be moved, concentrated and/or extracted through use of the methods of the invention are:

electrically charged or neutral biomacromolecules such as proteins, RNA, DNA, and suitable lipids; long polymers; polypeptides;

aggregations of molecules such as micelles or other supramolecular assemblies;

any particles to which magnetic beads or electrically-charged beads can be attached;

living microorganisms; and, the like.

For any particular type of particles, one can attempt to identify a suitable driving field, medium, and mobility-altering field. Since many biomacromolecules can be electrically charged, it is often suitable to use a time-varying electrical field as the driving field when applying the invention to moving and/or concentrating such particles. Further, there are well developed techniques for causing magnetic beads to bond to specific biological materials. Where it is desired to move and/or concentrate materials which can be caused to bond to magnetic beads then magnetic fields may be used as driving fields.

Media

The medium is selected to be a medium through which the particles can move and also a medium wherein the mobility of the particles can be altered by applying a suitable mobility-altering field. The medium may comprise, for example:

a gel, such as an agarose gel or a performance optimized polymer (POP) gel (available from Perkin Elmer Corporation);

a solution, aqueous or otherwise;

entangled liquid solutions of polymers;

viscous or dense solutions;

solutions of polymers designed to bind specifically to the molecules (or other particles) whose motion is to be directed;

acrylamide, linear poly-acrylamide;

micro-fabricated structures such as arrays of posts and the like, with spacing such that the particles of interest can be entangled or retarded by frequent collision or interaction with the micro-fabricated structure;

structures designed to interact with molecules by means of entropic trapping (e.g. Craighead et al., in Science 12 May 2000 Vol. 288);

high viscosity fluids such as Pluronic™ F127 (available from BASF);

water; or the like.

The medium is chosen to have characteristics suitable for the particles being moved. Where the particles are particles of DNA then suitable polymer gels are the media currently preferred by the inventors. In some specific embodiments of the invention the particles comprise DNA and the medium comprises an agarose gel or a suitable aqueous solution. In some embodiments the aqueous solution is a bacterial growth medium mixed with a gel such as an agarose gel.

2D Scodaphoresis

In some embodiments, the particles are constrained to move on a two-dimensional (2D) surface. In some embodiments the 2D surface is planar. The 2D surface is not necessarily planar. In some embodiments, the 2D surface comprises a relatively thin layer of a medium, such as a gel. In some embodiments the medium is free-standing. The medium may be supported on a substrate. The substrate may comprise a sheet of glass or a suitable plastic such as mylar, for example. In some embodiments the 2D layer of medium is sandwiched between the surfaces of two substrates. Where the medium has an exposed surface, the surface may be in air or another gaseous atmosphere or submerged in a liquid such as a suitable buffer, an oil, or the like. In some currently preferred embodiments, the medium comprises a layer of a gel sandwiched between two layers of thicker gel. In an example embodiment, particles move in a layer of a 1% w/v agarose gel sandwiched between two layers of 3% w/v agarose gel.

In some embodiments of the invention, a 2D surface in which particles travel may be provided by a layer within a medium which has a non-uniform viscosity or a non-uniform concentration of a species that reduces (or increases) a mobility of the particles. The viscosity or concentration gradient cause particles to remain in the relatively thin layer within the medium or on a surface of the medium.

3D Scodaphoresis

SCODA may be used to concentrate particles in three dimensions. This may be achieved in various ways. In some embodiments, 2D SCODA is performed in a plane. The 2D SCODA may be performed using the electrophoretic SCODA method described below, for example. Z electrodes placed above and below the plane could apply an electric field that tends to drive any particles that begin to move out of the plane back into the plane.

3D SCODA could also be performed by providing a 6 electrode arrangement, where each electrode is placed on the surface of a body of a medium such as a gel. Defining X Y and Z axes of such a cube, 2D SCODA would then be run on the 4 electrodes in the XY plane, then the 4 electrodes in the YZ plane, then the 4 electrodes in the XZ plane, then repeating in the XY plane and so forth. This would produce a net 3D focussing effect, with a net SCODA force that is radial in three dimensions, but about ⅓ as strong as the 2D SCODA force for the same electrode voltages.

Control Systems

Any suitable control mechanism may be used to cause a driving field and a mobility-varying field to be applied in a coordinated manner to cause particles to move by SCODA. In some embodiments of the invention, the time-variation of the driving field and the mobility-varying field are derived directly from a common source such that their effects on the particles are correlated. In other embodiments of the invention the driving and mobility-varying fields are generated under the control of a controller such as a hard-wired controller, a programmable controller, a general purpose computer equipped with suitable interface electronics or the like. Any suitable control mechanism including those known to those skilled in the art of designing scientific equipment may be applied.

EXAMPLES

The following examples illustrate various specific embodiments of the invention. These embodiments of the invention are considered to be individually inventive. Some of these examples summarize experiments that have been performed and others are prophetic examples.

Example 1

Electrophoretic Concentration of Particles by SCODA

Consider an electrically charged particle that has an electrophoretic mobility, $\mu$ in an electric field given by $\vec{E} = \cos(\omega t) E \hat{E}$, where $\hat{E}$ is a unit vector. By definition, the particle will move with a velocity given by:

$$\vec{v} = \mu \cos(\omega t) E_0 \hat{E} \qquad (9)$$

From Equation (9), $\vec{v}$ has a time average of zero. If $\mu$ varies as a function of time and the Fourier transform of $\mu$ has a component proportional to cos(ωt) then the time average of v(t) may not be zero. As a simple example, consider the case where:

$$\mu(t)=\mu_0+\mu_1 \cos(\omega t) \quad (10)$$

In this case, the time average of v(t) is:

$$\vec{v} = \frac{1}{2}\mu_1 E_0 \hat{E} \quad (11)$$

This demonstrates the basic principle that there can be a non zero electrophoretic drift even if the time average of the applied electric field is zero.

Now consider the case where the mobility of a particle is a function of electric field strength. While virtually any nonlinearity can be employed, consider the case where a particle's velocity is parallel to the direction of a driving electric field and the particle's speed is given by:

$$v=kE^2 \quad (12)$$

where k is a constant and E is the magnitude of the electric field. In this case, the particle's speed is proportional to the square of the magnitude of the electric field. The effective mobility of the particle (i.e. the relationship between small changes in drift velocity, $d\vec{v}$, and small changes in the electric field, $d\vec{E}$) varies with the magnitude of the applied electric field.

In Cartesian coordinates:

$$dv_x = \frac{\partial v_x}{\partial E_x}dE_x + \frac{\partial v_x}{\partial E_y}dE_y \text{ and} \quad (13)$$

$$dv_y = \frac{\partial v_y}{\partial E_x}dE_x + \frac{\partial v_y}{\partial E_y}dE_y$$

Where the particle speed varies with the electric field as in Equation (12), Equation (13) reduces to:

$$dv_x = k\left[\left(E + \frac{E_x^2}{E}\right)dE_x + \left(\frac{E_x E_y}{E}\right)dE_y\right] \quad (14)$$

$$dv_y = k\left[\left(\frac{E_x E_y}{E}\right)dE_x + \left(E + \frac{E_y^2}{E}\right)dE_y\right] \quad (15)$$

To help interpret this, consider the case where $E_y=0$ such that $E_x=E$. In this case Equations (14) and (15) become:

$$dv_x=2kEdE_x \text{ and } dv_y=kEdE_y \quad (16)$$

From Equation (16) one can see that the influence on the particle velocity of perturbations of the electric field has a magnitude proportional to that of the ambient field. A perturbation having the same direction as the electric field has twice the influence on the particle velocity as a perturbation perpendicular to the electric field.

This can be exploited to provide an applied electric field that causes particles to be concentrated. Consider a plane wherein an applied electric field has a constant magnitude, E and the electric field rotates in direction at an angular frequency ω so that the components of the electric field in x and y directions are given by:

$$E_x=E \cos(\omega t) \text{ and } E_y=E \sin(\omega t) \quad (17)$$

Substituting the values from Equation (17) into Equations (14) and (15) yields a result which is the sum of constant terms, sine and cosine terms having an angular frequency ω, and sine and cosine terms having an angular frequency 2ω. A frame of reference can be selected such that only the cosine terms having an angular frequency of 2ω contribute to net particle drift. Evaluating only these terms yields:

$$dv_x = \frac{kE}{2}[\cos(2\omega t)]dE_x \text{ and} \quad (18)$$

$$dv_y = \frac{kE}{2}[\cos(2\omega t)]dE_y$$

If a perturbing electric field having the form of a quadrupole field that varies with a frequency 2ω is added to the basic electric field specified by Equation (17) then a net drift of particles can be caused. For a perturbing electric field given by:

$$dE_x=-dE_q x \cos(2\omega t) \text{ and } dE_y=dE_q y \cos(2\omega t) \quad (19)$$

it can be shown that:

$$\overline{d\vec{v}} = \frac{kEdE_q}{4}\vec{r} \quad (20)$$

Equation (20) shows that for charged particles at all positions $\vec{r}$ there is a time-averaged drift toward the origin with a speed proportional to k, the coefficient that specifies the field-dependence of the mobility, E, the strength of the rotating field, and $dE_q$, the strength of the perturbing quadrupole field.

Figure 2:
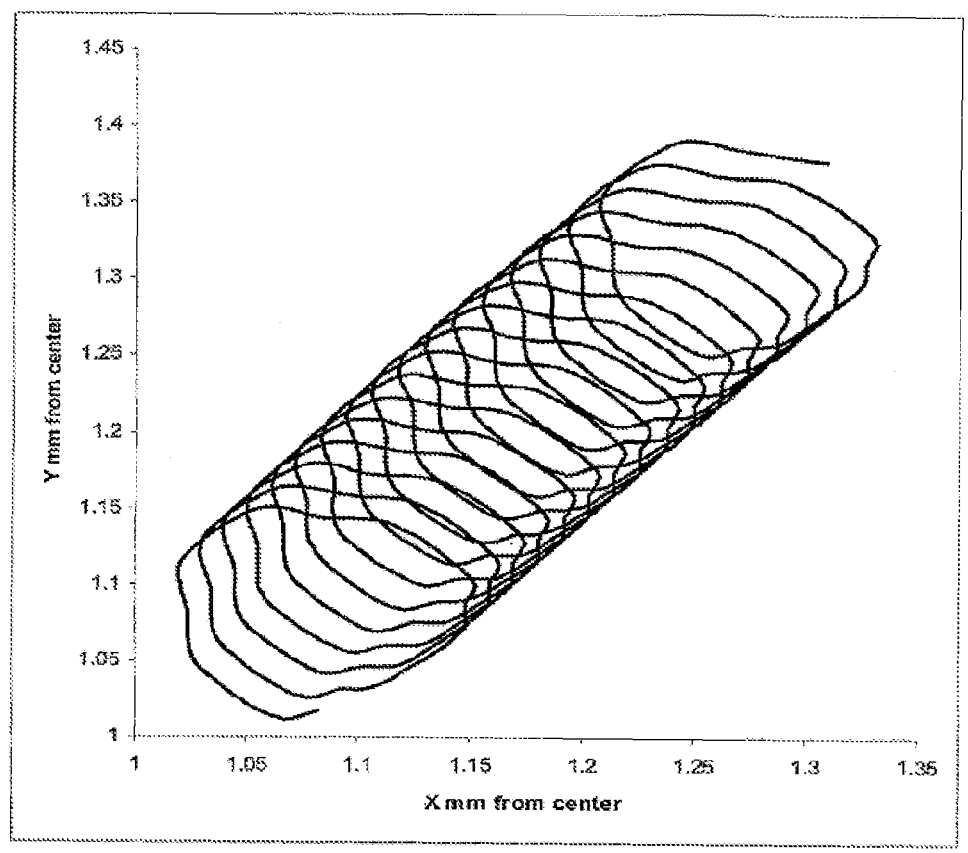
FIG. 2 is a plot showing a numerical simulation of the path of a particle.

The above calculation is for a case where the perturbing quadrupole field has a magnitude that is small in comparison to the rotating field. This is not necessary in general. FIG. 2 shows the result of a numerical simulation of the path of a particle in a case where the rotating electric field and quadrupole electric field are similar in magnitude. Motion begins at the top right hand side of FIG. 2 and progresses toward the bottom left over a period of 200 seconds. The applied electric fields are as described in Table I below. Each loop in the spiral path corresponds to a cycle of 12 voltage patterns each applied for 1 second. The uniform field amplitude is 3845 V/m at the origin (centre of the electrode pattern). At the same location, the magnitude of the quadrupole component of the electric field is $4.2 \times 10^5$ V/m$^2$ or about 4200 V/m at a location 1 mm from the origin.

In many situations it is advantageous to concentrate particles in regions that are free of electrodes. Electrochemical processes at electrodes can cause damage to DNA and other sensitive materials. An electrical field that provides a particle focussing effect, as described above, can be provided without the need for electrodes at the location in which the particles become concentrated.

One can estimate the size of the spot into which particles can be concentrated from the Einstein-Smoluchowsky equation for diffusion with drift. A characteristic length scale, R, for the radius of a concentrated spot is given by:

$$R \propto \sqrt{\frac{D}{\mu s}} \quad (21)$$

where D is the diffusion coefficient for the particles and $\mu_s$ is given by $kEE_q/4$.

Figure 3:
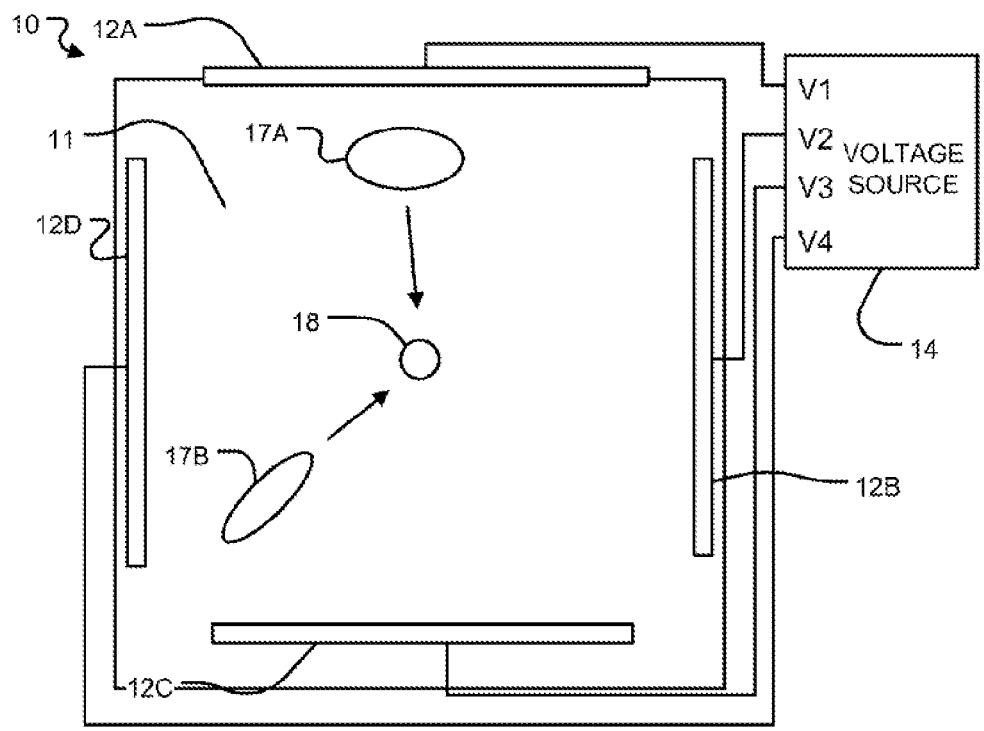
FIGS. 3, 3A, 3B, 3C and 3D are schematic diagrams of apparatus that may be used to practice embodiments of the invention.

FIG. 3 shows apparatus 10 having a simple arrangement that can be used to practice the invention. A layer 11 of a medium, which may be a gel, such as an agarose gel, is located between four symmetrically arranged electrodes 12A, 12B, 12C and 12D (collectively electrodes 12). It has been found to be desirable to provide electrodes 12 in the form of mesh electrodes. A power supply 14 applies individually controllable electrical potentials V1, V2, V3 and V4 to electrodes 12A through 12D respectively. Since it is the relative potentials of electrodes 12A through 12D that is significant, any one of electrodes 12A to 12D may be held at a convenient fixed voltage, such as 0 volts, while the voltages applied to the other electrodes are varied, if desired.

Figure 3A:
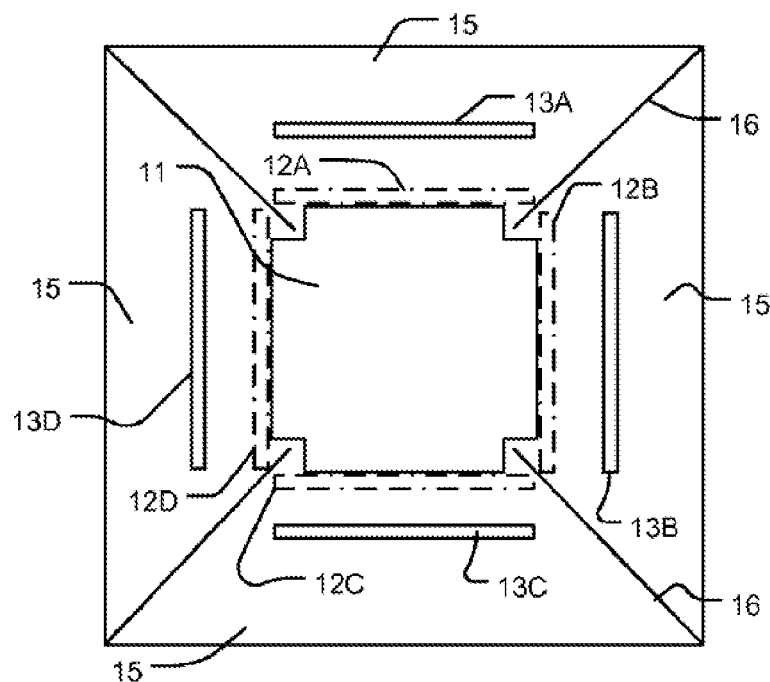

It is generally desirable to control the potentials applied to the electrodes to help stabilize the electric stimuli against small fluctuations due to changing temperature or changing power supply characteristics. Separate electrical potential sensing electrodes may be incorporated to provide feedback to a controller representing the actual electrical potential being applied. FIG. 3A is a schematic view of an apparatus comprising mesh electrodes 12A, 12B, 12C and 12D and separate potential sensing electrodes 13A, 13B, 13C and 13D (collectively electrodes 13). Large buffer reservoirs 15 maintain an ample supply of buffer against evaporation for long runs. Insulating barriers 16 separate adjacent reservoirs 15 electrically. Electrodes 13 are located in buffer reservoirs 15 and monitor the potential in the buffer. Feedback from electrodes 13 allows a suitably configured controller 14 to automatically adjust the voltages on mesh electrodes 12 to compensate for varying voltage drops across the mesh electrodes/buffer interface.

The magnitude of the applied voltage is chosen to match the size of the apparatus and the particles being separated. For DNA separations in agarose gels electric driving fields of approximately 50V/cm have been found to give satisfactory performance. The current supplied will depend upon the electrical conductivity and dimensions of the medium.

The application of the potentials causes electrically charged particles in medium 11 to move toward a central region 18. FIG. 3 shows groups 17A and 17B of particles moving toward concentration region 18. As noted above, the precise waveform according to which the applied electric fields vary is not critical to the operation of the invention. In a prototype embodiment of the invention, the potential variation of Equations (16) and (18) was approximated by a series of patterns of discrete voltages applied to electrodes 12A through 12D. In the prototype, each cycle was made up of 12 patterns that were each applied for 1 second before moving to the next pattern. Table I shows the voltages applied for each pattern.

TABLE I

| | Voltage Patterns | | | |
|---|---|---|---|---|
| Pattern | Electrode 12A (V) | Electrode 12B (V) | Electrode 12C (V) | Electrode 12D (V) |
| 1 | 0 | −66 | 0 | −198 |
| 2 | 132 | 132 | 0 | 0 |
| 3 | 132 | 198 | 0 | 198 |
| 4 | 132 | 198 | 0 | 198 |
| 5 | 132 | 0 | 0 | 132 |
| 6 | 0 | −198 | 0 | −66 |
| 7 | 0 | −198 | 0 | −66 |
| 8 | −132 | −132 | 0 | 0 |

TABLE I-continued

| | Voltage Patterns | | | |
|---|---|---|---|---|
| Pattern | Electrode 12A (V) | Electrode 12B (V) | Electrode 12C (V) | Electrode 12D (V) |
| 9 | −132 | 66 | 0 | 66 |
| 10 | −132 | 66 | 0 | 66 |
| 11 | −132 | 0 | 0 | −132 |
| 12 | 0 | −66 | 0 | −198 |

Figure 3B:
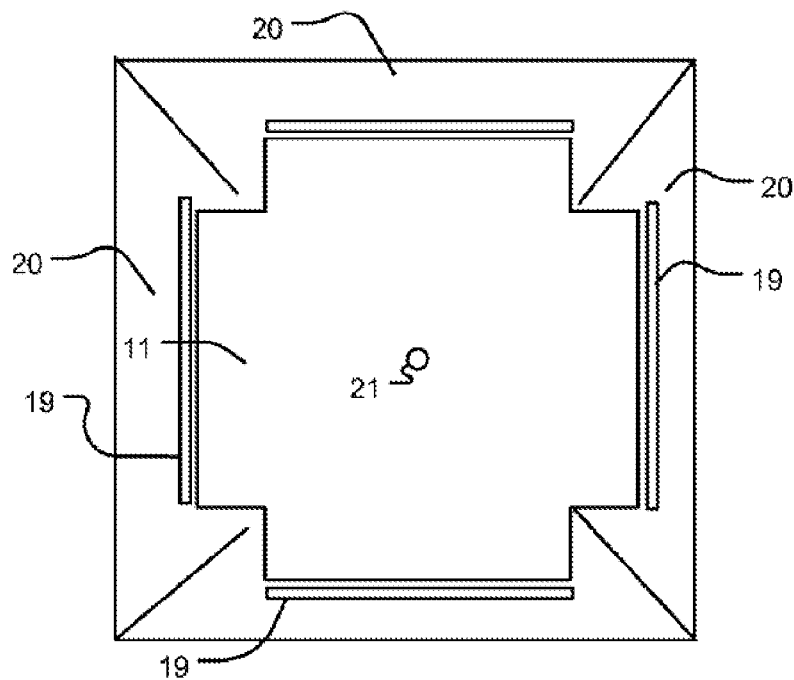

In the prototype embodiment of the invention illustrated schematically in FIG. 3B, medium 11 was in the form of a gel slab made up of 8-11 ml of 0.25% agarose gel (Agarose 2125 OmniPur available from EMD Chemicals of Gibstown N.J., USA) forming a 3.8 cm square on an acrylic base in a 0.1×Tris-acetate-EDTA buffer. Four electrodes were submerged in the gel. Each electrode extended across one third of one side of the gel boat approximately 2.5 mm up from the bottom of the gel boat. DNA was prepared by mixing 8 µl of 500 µg/ml λ phage DNA (48,502 bp, part No. N3011L available from New England Biolabs of Beverly Mass., USA) with 12 µl 0.1×TAE. 5 µl spots of the DNA were pipetted directly onto the gel after the gel had set. A thin covering of TAE was placed on the gel. The voltage patterns of Table I were applied to the electrodes. It was found that the DNA spots were all carried to a central area of the gel.

Figure 4:
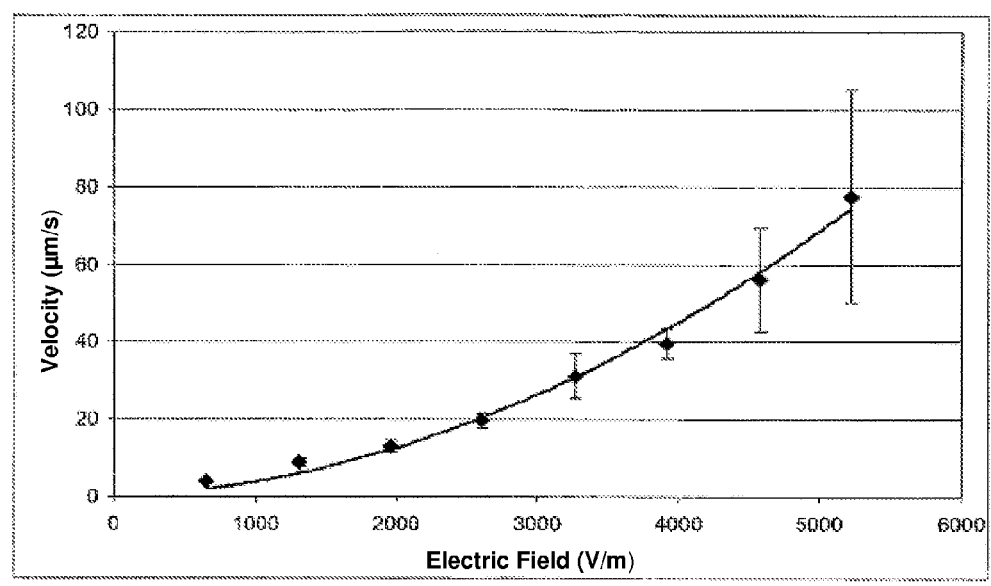
FIG. 4 is an example plot of measured DNA velocity as a function of applied electric field.
Figure 4A:
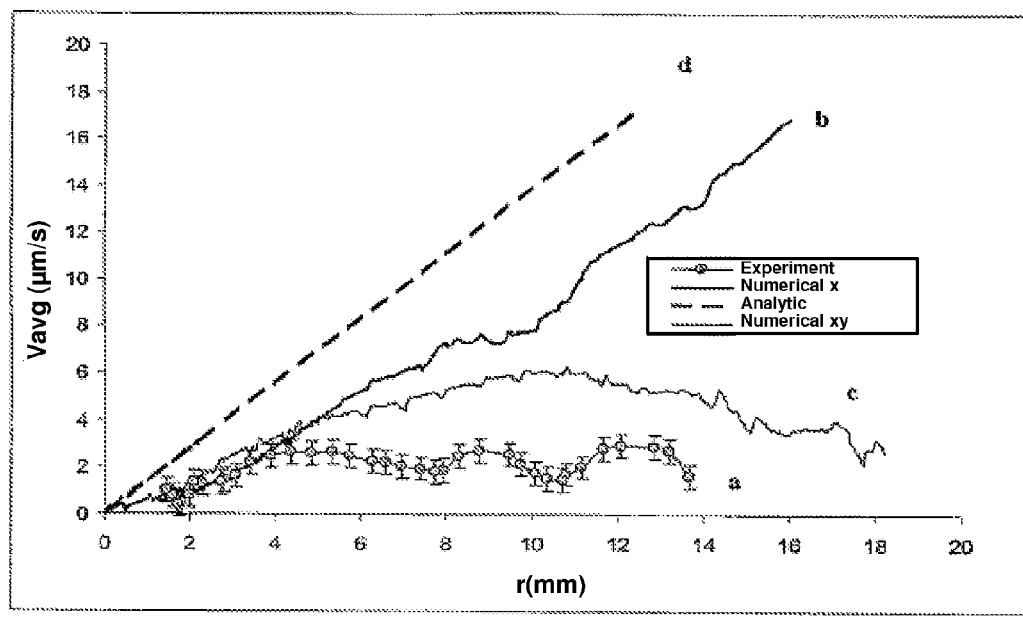
FIG. 4A is a plot illustrating time averaged particle velocity in an apparatus like that of FIG. 3 as a function of radial distance from the origin.

FIG. 4 is an example plot of measured DNA velocity as a function of applied electric field for the λ DNA used in the prototype embodiment. FIG. 4A is a plot showing time averaged drift velocity (averaged over 15 minutes) of the DNA as a function of the radial distance from the origin to which the DNA converged. FIG. 4A includes curve 21A which is a numerical estimate of the trajectory of a particle starting at a location on the X-axis and curve 21B which is a numerical estimate of the trajectory of a particle starting at a location X=Y=1.5 cm from the origin.

Figure 4B:
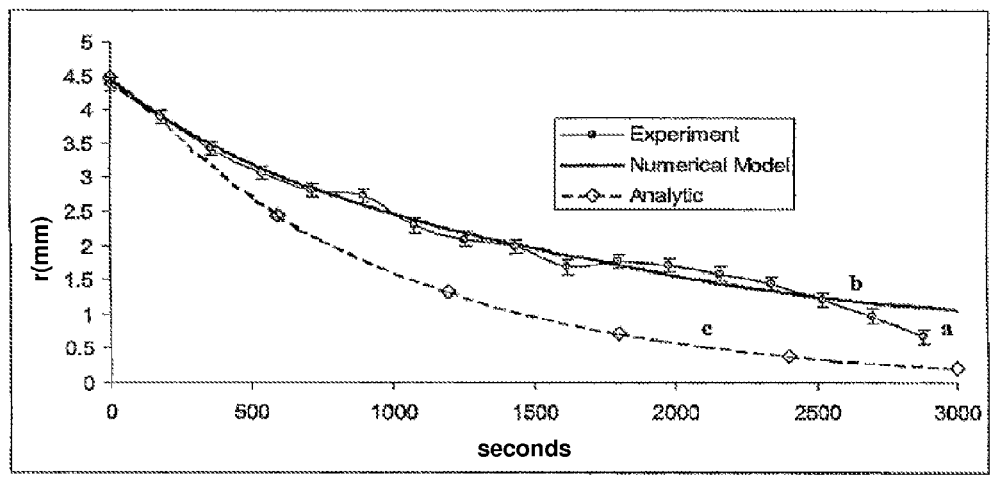
FIG. 4B is a plot showing the measured DNA spot distance from the origin as a function of time.

FIG. 4B is a plot showing the measured DNA spot distance from the origin as a function of time compared to numerical and analytical predictions. The spot position is measured over all spots visible in a given time interval. Spot trajectories for spots starting at different radial distances from the origin are shifted in time so that the start time for spots starting closer to the origin is replaced by the time at which spots starting farther from the origin reach the starting locations of the spots closer to the origin.

In the regime illustrated in FIG. 4B, there was good agreement between the calculated and observed spot trajectories.

For the DNA used in the prototype, D was measured experimentally to be $2 \times 10^{-12}$ m$^2$/s. $\mu_s$ was measured to have a value of approximately $1 \times 10^{-3}$ 1/s. Using these values, the limiting spot size was calculated to be on the order of 100 µm. Spot radii on the order of 150 to 250 µm have been achieved in experiments.

In another experiment, a homogeneous solution of 400 ng/ml λ DNA in 1% agarose gel (0.01×TAE) was subjected to scodaphoresis. The gel was prepared by mixing 3 ml of 1% agarose gel with 1.5 µl of 500 ng/µl 48,502 bp λ DNA and 1.5 µg ethidium bromide (500 ng/ml final concentration). The gel was allowed to cool to approximately 65° C. and then poured into the gel boat. The gel was arranged in a cross shape, as shown in FIG. 3B. Platinum electrodes 19 0.03 mm in diameter were located in open electrode regions 20 of the apparatus. The electrode regions were free from gel and filled with 0.01×TAE buffer.

The distance between opposing electrodes was approximately 2.4 cm. After approximately 90 minutes, the λ DNA was found to have been concentrated in a region 21 in the centre of the gel boat in a spot having a full width at half maximum of about 300 μm. The concentration of the λ DNA in the spot was enhanced by a factor of approximately 3000 to 4000 as compared to the initial concentration of λ DNA in the gel boat. The ability to cause DNA to be concentrated in an area 21 which is away from electrodes is advantageous in various applications.

The concentration factor, F, that can be achieved using a square gel slab having sides of length L is calculated to be approximately:

$$F = \frac{1}{\pi}(L/200 \text{ μm})^2 \qquad (22)$$

Therefore, other factors being equal, increasing the dimensions of the gel slab can increase the concentration factor. For example, calculations suggest that a 35 cm×35 cm square gel slab could produce a concentration factor on the order of $10^6$. To achieve the best concentration it may be desirable to take steps to inhibit diffusion of particles out of the 2D surface in which SCODA is being used to concentrate the particles.

Electrophoretic SCODA in two dimensions can be performed conveniently using four electrodes arranged in two opposing pairs, as described above. Other arrangements of three or more electrodes that are not collinear with one another could also be used. For example SCODA could be performed using three electrodes arranged at corners of a triangle. SCODA could also be performed using five or more electrodes arranged around a region of a medium.

Since the passage of electrical current through a medium can lead to heating of the medium and most practical media are electrically conducting to some degree it is desirable to design SCODA apparatus to minimize heating, where practical, and to ameliorate the effects of heating, where necessary. For example, SCODA may be practised in ways which include one or more of:

- cooling the medium through the use of a cooler in physical contact with the medium, cooling a buffer circulating around the medium, blowing cool air over the medium or evaporatively cooling the medium;
- making the medium very thin, thereby reducing the electrical current flowing in the medium and improving dissipation of heat from the medium;
- placing the medium on a thermally-conductive substrate that acts as a heat sink;
- reducing the electrical conductivity of the medium by way of a chemical treatment or by separating from the medium unneeded species that give rise to increased electrical conductivity;
- providing a reservoir of buffer and replenishing buffer surrounding the medium as the buffer evaporates (see, for example, FIG. 3A);
- providing one or more temperature sensors that monitor temperature of the medium and controlling the temperature of the medium to remain within an acceptable range by controlling the electrical current supplied to electrodes; and,
- using a driving field other than an electrical field.

Example 2

3D SCODA

Figure 3C:
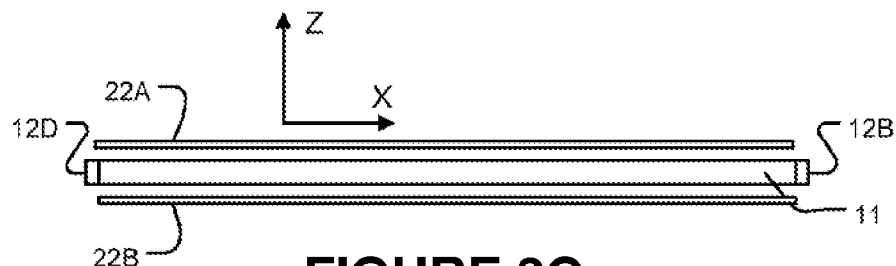

FIG. 3C shows apparatus similar to that of FIG. 3 that has been modified by the provision of additional Z electrodes 22A and 22B. Z electrodes 22A and 22B are each maintained at a DC voltage. For negatively charged particles, Z electrodes 22A and 22B are kept more negative in potential than the 2D SCODA electrodes 12A, 12B, 12C, and 12D. The provision of the Z electrodes provides a focussing force in the Z axis, and a de-focussing force in the XY plane of medium 11. The defocussing force is counteracted by SCODA.

Example 3

3D SCODA

Figure 3D:
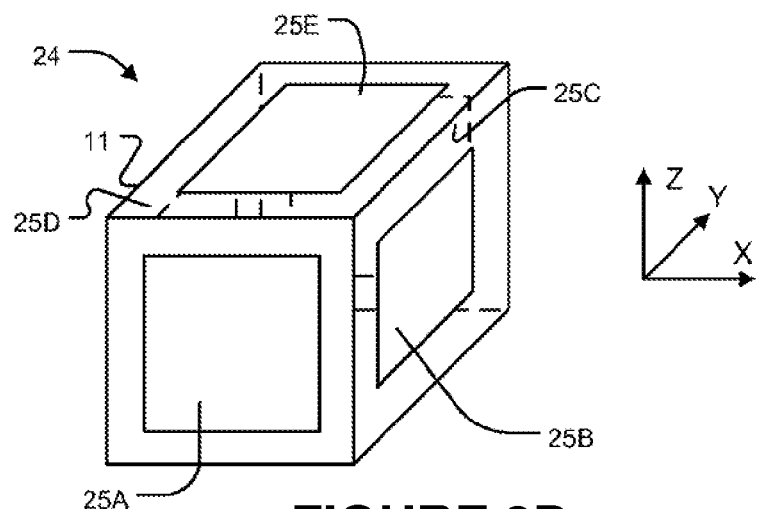

FIG. 3D shows apparatus 24 according to an embodiment of the invention that provides 3D concentration of particles in a cube-shaped block of medium 11 by alternately performing SCODA using electrodes in XY, XZ, and YZ planes. For example, electrodes 25A, 25B, 25C, and 25D are used for concentration in the XY plane. Electrodes 25A, 25E, 25C and another electrode (not visible in FIG. 3D) on the side of medium 11 opposed to electrode 25E are used for concentration in the YZ plane. Electrodes 25B, 25E, 25D and the electrode opposed to electrode 25E are used for concentration in the XZ plane.

Example 4

Size Selection by SCODA

If desired, SCODA processes can be made to select DNA and similar particles by size. This may be achieved by suitably adjusting the diffusion coefficient, D (D can be controlled by choice of medium), and the frequency of the driving field. Using higher driving field frequencies can cause larger particles to be less likely to be concentrated by SCODA. For example, in one experiment applying a driving field having a period of 12 seconds was found to concentrate both long λ DNA and shorter DNA fragments from a 1 kB ladder. It was found that reducing the period of the driving field to approximately 10 ms resulted in concentration of only the shorter DNA fragments but not the longer λ DNA fragments. While the inventors do not wish to be bound by any particular theory of operation, this size selection may be due to the 10 ms period being shorter than the relaxation time for the larger λ DNA fragments and longer than the relaxation time for the shorter DNA fragments.

In the same experiment it was found that SCODA did not concentrate shorter DNA fragments (smaller than a few hundred bp). The selection out of the small sizes may be due to the smaller fragments having higher values for the diffusion coefficient D.

It is believed that SCODA provides a method for separating supercoiled plasmids from plasmids that are nicked or otherwise degraded.

Example 5

Purification of DNA

Because SCODA can be made selective for different kinds of particles by choosing a suitable medium and/or combination of driving and mobility-varying fields, SCODA can be used to purify materials, such as DNA. SCODA can be applied to cause DNA (or optionally DNA having a particular size range) to concentrate at a spot or along a line while other materials are not concentrated at the spot or line.

For example, in initial experiments, λ DNA was concentrated from a mixture of λ DNA and bovine serum albumin (BSA). There was a 10:1 concentration ratio of BSA to λ DNA. The λ DNA was concentrated into a spot, as described above. The BSA was not concentrated in the spot.

In some embodiments of the invention, denaturing agents, protease, nuclease inhibitors and/or RNAase are added to a mixture of materials from which the particles are to be separated. Such agents may be provides to facilitate one or more of:

reducing the binding of undesired molecules to fragments of DNA or other molecules that are desired to be concentrated;
reducing the amount of RNA present, if so desired;
preventing damage to DNA; and/or
breaking down the undesired molecules into components that will not be concentrated by SCODA.

In some cases it may be desirable to use SCODA to separate particles of interest from a mixture which includes materials, such as salts, that cause the medium a high electrical conductivity. For example, bacterial cell cultures are often grown in media having salt contents on the order of up to 0.4M. In cases where it is desired to use electrophoretic SCODA to separate DNA directly from a cell culture, such as an *E. coli* culture, the high electrical conductivity will result in higher electrical currents in the medium. This in turn can lead to heating of the medium. This issue may be addressed by one or some combination of the heating control techniques discussed above.

Example 6

SCODA with Selective Media

The mobility of a particle in a medium may be made dependent upon the presence in the particle of a specific DNA sequence by providing a medium with which DNA interacts by binding interactions. For example, a gel may be made to include DNA oligonucleotides that are complementary to the DNA in the particles that it is desired to concentrate. The complementary DNA oligonucleotides may be covalently bonded to the gel.

If the characteristic time required for the particles to bind to the complementary DNA oligonucleotides is $t_{on}$ and the characteristic time required for the particles to dissociate from the DNA oligonucleotides is $t_{off}$ then the average drift velocity for a particle in the medium is given by:

$$\bar{v} = \mu(E) * E \frac{t_{on}}{t_{on} + t_{off}} \quad (23)$$

where $\mu(E)$ is the field-dependent particle mobility due to reptation effects. Typically, $t_{off}$ is determined by an Arrhenius relationship while $t_{on}$ is determined by diffusive effects. By selecting particles to have lengths of 1000 or more nucleotides, reasonable values for $t_{off}$ of 1 second or less can be achieved with practical values of electric field (for example, electric fields in the range of 100 to 200 V/cm).

Figure 5:
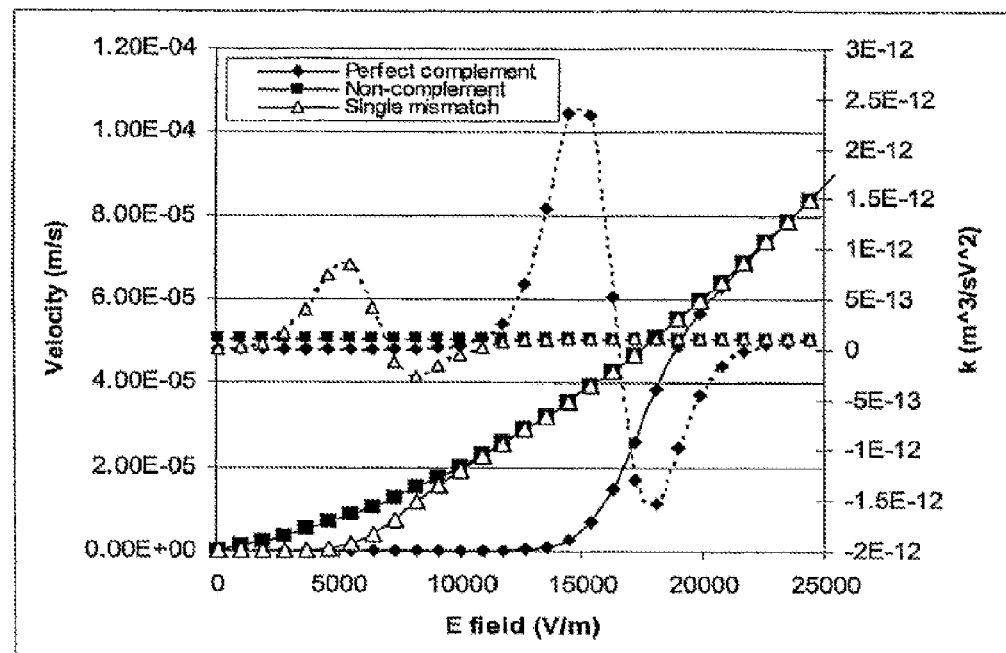
FIG. 5 shows estimated particle velocity as a function of electric field strength for three molecules in a sieving matrix comprising covalently bound oligonucleotides.

FIG. 5 shows estimated particle velocity as a function of electric field strength for three molecules in a sieving matrix comprising covalently bound oligonucleotides. A first one of the molecules is a perfect match to the covalently-bound oligonucleotides, a second one of the molecules has a single nucleotide mismatch to the covalently-bound oligonucleotides and a third one of the molecules is non-complementary to the covalently-bound oligonucleotides. DC velocity is shown in solid lines. The SCODA mobility $\mu_s$ is shown in dashed lines.

It can be seen that there are values for the electric field that result in the SCODA mobility for particles having DNA that binds to the covalently bound oligonucleotides being significantly greater than for other particles. At the electric field identified by line 7 the SCODA mobility for particles that perfectly complement the covalently bound oligonucleotides is 25 times greater than it is for non-complementary and single nucleotide mismatch molecules.

Example 7

Electric Driving Field and Thermal Mobility Varying Field

A demonstration of SCODA was carried out by thermally altering the drag coefficient of current-carrying solute ions in an electrolyte. When applying an AC potential across an electrolyte solution, and synchronously raising and lowering the temperature of the solution, a net transport of ions is expected. If the oscillation frequency of the AC potential differs from the frequency of the thermal oscillations, a detectable component of the ionic current should be present at the difference of the two frequencies, indicating alternating (AC) transport due to SCODA.

Figure 6:
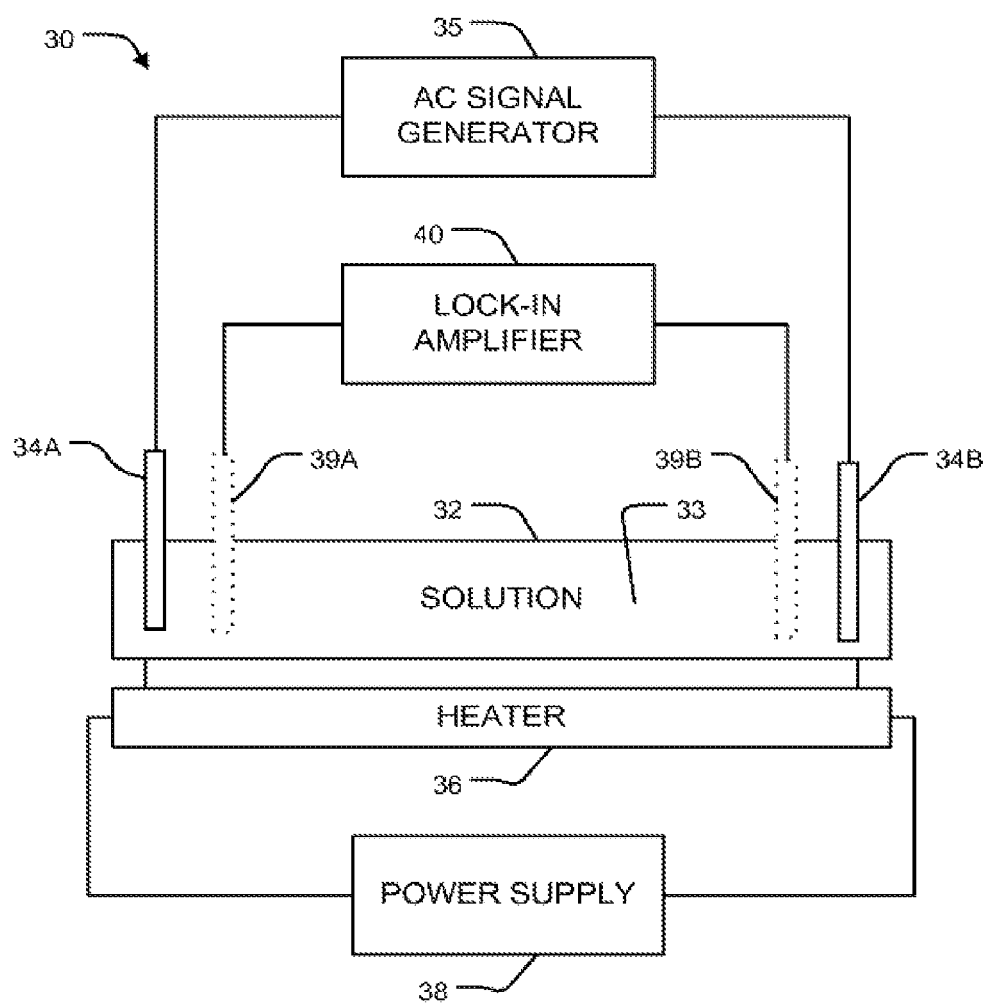
FIG. 6 is a schematic diagram of apparatus that may be used to explore scodaphoresis using an electric driving field and a thermal mobility-varying field.

FIG. 6 shows apparatus 30 that may be used to explore electric-thermal scodaphoresis. Apparatus 30 comprises a chamber 32 holding an ionic solution 33. Electrodes 34A and 34B are immersed in solution 33. A signal generator 35 applies an electrical signal of a first frequency between electrodes 34A and 34B. A heater 36 is in thermal contact with solution 33. Heater 36 is driven by a power supply 38 so that the temperature of solution 33 is made to vary at a second frequency different from the first frequency. A detector 40 such as a lock-in amplifier is connected to electrodes 39A and 39B. Detector 40 detects a signal at a frequency equal to the difference of the first and second frequencies.

In an experimental prototype apparatus, a microscope slide, cover slip and epoxy were used to construct a chamber holding 300 μL of 2.0M NaCl solution. Two gold wire electrodes were glued to the microscope slide 1 cm apart such that they were immersed the NaCl solution. One of the electrodes was grounded and the other connected through a 1 kΩ resistor to an AC amplifier. Nickel-Chromium Alloy wire (NIC60-015-125-25, Omega, Stamford, Conn.) was glued to one side of the microscope cover slip to allow heating of the solution.

During operation, 1.32 A of current was pulsed to the heater in the form of a 50% duty cycle, square wave at 10 Hz. A small fan running continuously was used to cool the microscope slide during off cycles of the heater. A 12 Hz, $3.0V_{RMS}$ sine wave was applied across the resistor and electrodes. These two signals were mixed and the output difference frequency (of 2 Hz) was fed into the reference input of a lock-in amplifier (SR830 DSP, Stanford Research Systems, Sunnyvale, Calif.). To measure the periodic current resulting from SCODA, the voltage across the 1 kΩ resistor was measured with the lock-in amplifier and the 2 Hz component was singled out for analysis. An ionic current oscillating at 2 Hz was detected.

The driven temperature oscillation of the sample solution was measured directly by a thermocouple (0.005-36, Omega) glued to the microscope slide between the electrodes. The 2 Hz component of the thermocouple output was also analysed using the lock-in amplifier.

We assume the temperature dependent change of the electrolyte's resistance $R_0$ is small compared to both the 1 k$\Omega$ current-monitoring resistor and the DC resistance of the solution ($R_{DC}$). The voltage across the electrodes is:

$$V = V_0 \cos(\omega_1 t), \quad (24)$$
$$V = 4.23\ V,$$
$$\omega_1 = \frac{2\pi}{T_1},$$
$$T_1 = \frac{1}{12}\ \text{sec}$$

The resistance of the salt solution is $R=R_{DC}+R_0 \cos(\omega_2 t+\phi)$ where the frequency of the induced thermal oscillation is $\omega_2=2\pi/T_2$ with $T_2=\frac{1}{10}$ s. The total current through the solution is then:

$$I_{TOT} = \frac{V_0 \cos(\omega_1 t)}{R_{DC}+R_0 \cos(\omega_2 t+\phi)} \quad (25)$$

Assuming $R_0$ is small, Equation (24) yields an expression with a sinusoidal term at the difference frequency $(\omega_2-\omega_1)$ whose amplitude is given by:

$$I = \frac{V_0 R_0}{2 R_{DC}^2} \quad (26)$$

A current having a magnitude of 4 μA at 2 Hz was observed.

Example 8

Electric Driving Field and Optical Mobility Varying Field

In some cases, one can alter the mobility of particles that it is desired to move by exposing the particles to radiation. In such cases one can practice scodaphoresis by controlling the application of radiation in time with the driving field such that the average mobility of the particles is different for the two directions of the driving field. For example, one could:
  apply radiation while the driving field is forcing the particles in one direction and not apply the radiation when the driving field is forcing the particles in the opposite direction;
  apply radiation of one wavelength or polarization when the driving field is forcing the particles in one direction and apply radiation of a different wavelength or polarization when the driving field is forcing the particles in the opposite direction;
  apply radiation of one intensity while the driving field is forcing the particles in one direction and apply radiation of a reduced intensity when the driving field is forcing the particles in the opposite direction;
  apply radiation having a time-varying intensity g(t) that has a non-zero correlation with the driving field;
  and so on.

In some cases it is not practical or desirable to use radiation to alter the mobility of the particles themselves but it is practical to bind to the particles other molecules that have mobilities that can be controlled by applying radiation. The other molecules may, for example, have conformations that can be changed by applying radiation or may bind to the medium in a manner that can be controlled by applying radiation.

Figure 7:
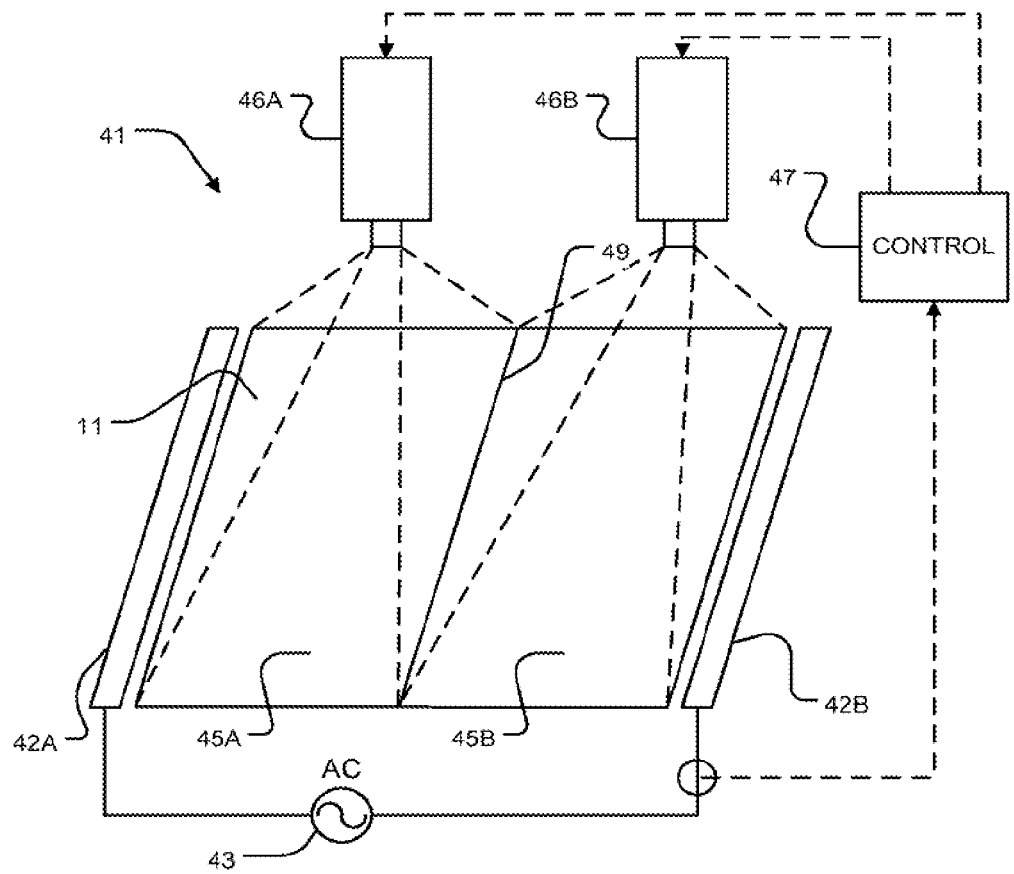
FIG. 7 is a schematic diagram of apparatus that may be used to explore scodaphoresis using an electric driving field and an optical mobility-varying field.
Figure 7A:
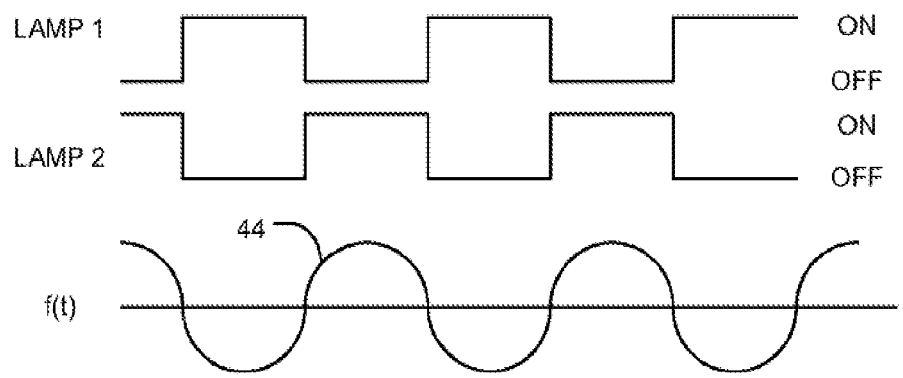
FIG. 7A shows waveforms from the apparatus of FIG. 7.

In some embodiments, azo-benzene is attached to particles to be subjected to scodaphoresis. Azo-benzene can isomerize from the trans- to cis-form upon exposure to UV light (300-400 nm). The azo-benzene reverts to its trans-form when it is exposed to light having a wavelength greater than 400 nm. In some embodiments, spiro-pyrans is attached to the particles. Exposure of the 'closed' form of spiro-pyrans to UV light induces isomerization to yield an 'open' coloured merocyanine species. The spiro-pyrans reverts to its 'closed' form on exposure to visible radiation. The transition between these two forms is accompanied by changes in the polar nature of the molecule.

Where radiation is used to vary the mobility of particles, different radiation fields may be applied in different areas to achieve concentration of the particles. For example, consider the apparatus 41 shown in FIG. 7. In apparatus 41 a medium 11 is located between two electrodes 42A and 42B. An AC power supply 43 applies an AC electrical signal 44 (FIG. 7A) between electrodes 42A and 42B.

Light projectors 46A and 46B respectively illuminate portions 45A and 45B of medium 11. A control 47 causes light projector 46A to illuminate area 45A only when signal 44 creates an electrical field in a first direction. Control 47 causes light projector 46B to illuminate area 45B only when signal 44 creates an electrical field in a second direction opposed to the first direction. The result is that particles in medium 11 converge on line 49 at the boundary of areas 45A and 45B from both sides.

Many alternative constructions can be used to illuminate areas 45A and 45B in time with a driving field. For example:
  Light from a single lamp could be steered by a suitable optical system to illuminate areas 45A and 45B in alternation;
  Light from one or more lamps could be blocked from areas 45A and 45B in alternation by a suitable arrangement of mechanical or electromechanical filters, shutters, masks or other devices having a controllable light transmission or reflection; and,
  so on.
Focussing in the Y direction may be achieved by rotating the light pattern and electrical field by 90 degrees relative to medium 11.

Electrical/optical SCODA may be used to cause particles to congregate at an array of spots or along a number of lines. This can be achieved by applying a patterned light field to the area of medium 11. This may be used to provide samples of DNA that are concentrated along spots or lines for example. Various biological applications require an array of spots or lines of DNA.

FIGS. 8A through 8D shows a possible arrangement of four masks 50A through 50D that can be used to concentrate particles into an array of 16 spots. Masks 50A and 50B are complementary to one another. Masks 50C and 50D are complementary to one another. Mask 50A is applied while a driving field causes particles to move in a direction 51A. Mask 50B is applied when the driving field causes particles to move in direction 51B. It can be seen that particles will be concentrated along the four lines 52A, 52B, 52C, and 52D if the driving field is alternated between directions 51A and 51B while masks 50A and 50B are applied as described above. Similarly, by alternately applying mask 50C with the driving field in direction 51C and mask 50D with the driving field in direction MD, particles will be concentrated along the four lines 53A, 53B, 53C, and 53D.

Figure 8E:
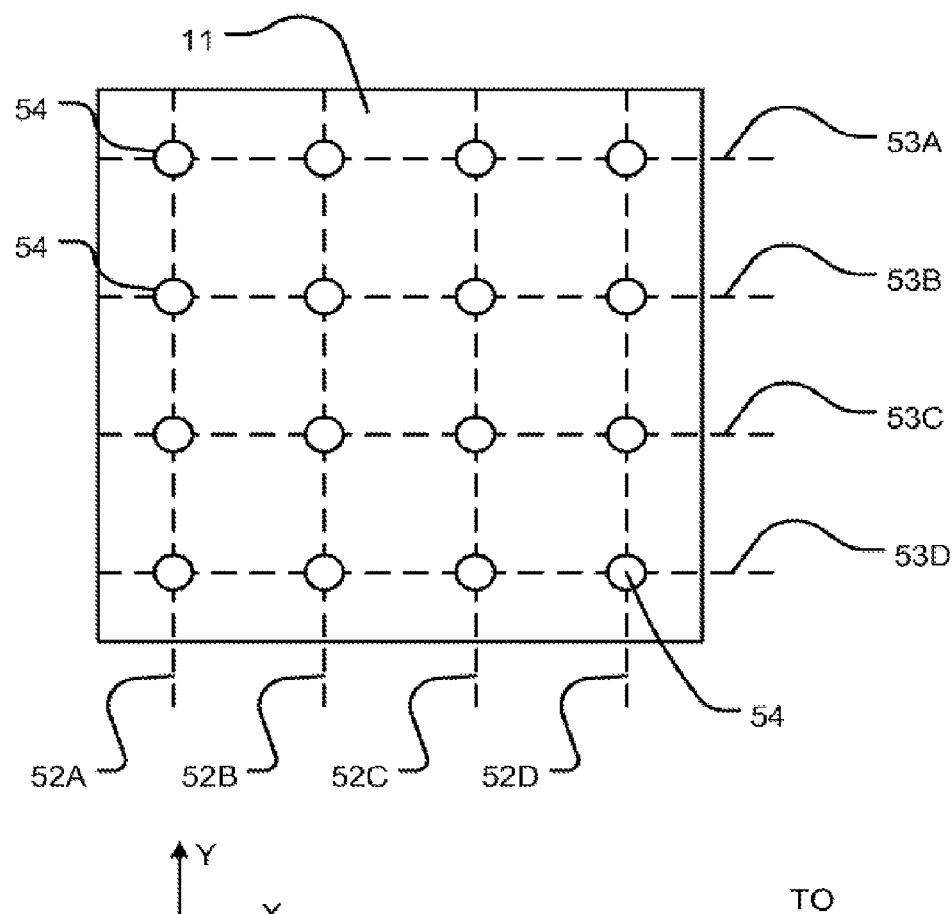
FIG. 8E shows an array of spots at which particles can be concentrated using the masks of FIGS. 8A through 8D.

Eventually, after a number of cycles, particles will be concentrated in spots 54 at the intersections of lines 52A to 52D and lines 53A to 53D as shown in FIG. 8E. The particles may comprise, for example, desired DNA or other molecules having attached azobenzene groups. The order in which masks 50A to 50D are applied (together with their corresponding driving fields) can be varied. In simple embodiments, concentration in the X direction is performed first using masks 50A and 50B and then concentration is performed in the Y direction using masks 50C and 50D.

Example 9

Optical Mobility Variation by Localized Viscosity Change

Particles to be concentrated by SCODA are located in a medium having a viscosity that varies with temperature. The mobility of the particles is dependent on the viscosity of the medium. The particles have an absorption band. Upon absorbing radiant energy having a wavelength in the absorption band, the particles release the absorbed energy as heat.

An alternating driving field of any suitable type is applied to the particles. The particles are illuminated with radiation having a wavelength in the absorption band and an intensity g(t). g(t) is selected so that g(t) has a non-zero correlation with the force f(t) applied to the particle by the driving field. When g(t) has a large value, the rate at which each particle releases thermal energy is larger than it is when g(t) has a smaller value. The thermal energy released by the particles in response to the absorbed radiation heats the surrounding media and locally alters its viscosity and thus the particle mobility.

Example 10

Fluid Flow as Driving Field

A SCODA driving field may be created by causing the medium in which the particles are situated to have a velocity that alternates in direction. For example, the medium may comprise a fluid in a pipe or capillary tube that is caused to flow back and forth in the pipe. The mobility of the particles may then be varied, either by causing the particles to interact with an externally applied field or by causing the particles to interact with a wall of the pipe in which they are located.

For example, consider a back and forth flow of a liquid in a pipe, in which molecules are suspended whose size is comparable to the pipe diameter (e.g. large DNA in a micron size capillary). Now, vary the capillary diameter (e.g. by providing the capillary with flexible walls such as walls of a silicone material and subjecting the capillary to external pressures) such that when the flow is in one direction, the molecules interact more frequently with the capillary wall and are retarded.

Example 11

Use of Cyclic Dilution/Concentration to Vary Mobility

Cyclic dilution/concentration may be used to vary the mobility of particles, especially where the particles are travelling along at or near a surface. The concentration or viscosity of the medium in which the particles are travelling may be modulated over time to correlate with the electrical or other field driving motion of the particles.

Figure 9:
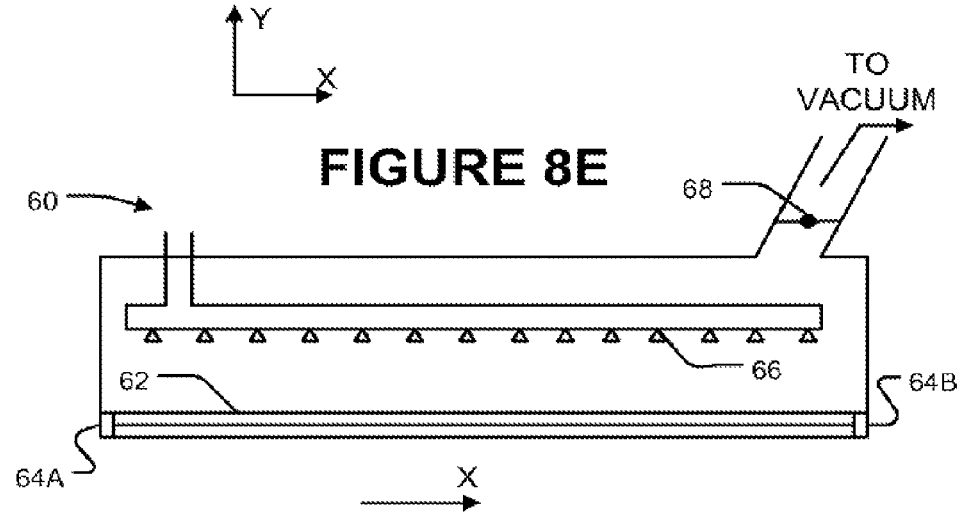
FIG. 9 is a schematic view of apparatus for producing cyclic variations in viscosity of a medium.

FIG. 9 shows apparatus 60 in which particles are travelling along a fluid layer 62. The particles are driven by an alternating electric field applied between electrodes 64A and 64B. A sprayer 66 dilutes fluid layer 62 by applying a solvent when the electric field is in a first direction. A vacuum valve 68 is opened to cause solvent from fluid layer 62 to evaporate, thereby increasing the concentration of fluid layer 62 when the electric field is in a second direction. Valve 68 and sprayer 66 are operated by a suitable control system (not shown).

Example 12

Pathogen Detection

In environmental sampling it is sometimes necessary to determine whether certain pathogens are present within relatively large volumes (e.g. 1 L or 10 L) of fluid (or solid material that can be dissolved in a fluid). Such volumes are too large for PCR to be performed in a cost effective manner in most cases. Filters can be used to concentrate DNA but such filters tend to clog. SCODA may be used to concentrate such pathogens, if present, in a sample. The sample can first be coarsely purified, then introduced into a medium in which particles of interest in the sample can be concentrated by scodaphoresis. For example, the particles may be introduced into a gel by mixing the sample with buffer and gel material to form a large volume gel. The buffer may include detergents or other agents to help lyse the pathogens and release their DNA into solution.

2D or 3D SCODA can them be performed to concentrate all or most of the DNA in the volume at a central location. The DNA at the central location is contained in a volume of gel that is manageable by normal means. The concentrated DNA may then be PCR amplified to detect specific pathogens. DNA can optionally be extracted from the gel using, for example, a commercial kit (e.g. Qiagen™) or using the I-ZIFE extraction methods described below before performing PCR amplification. In the alternative, a piece of the gel including the concentrated DNA may be subjected to PCR. The gel tends to melt during the PCR reaction does not significantly adversely affect the PCR amplification in some applications.

Example 13

Magnetic Control of Particle Mobility

FIG. 10A shows a medium 60 comprising a polymer matrix. The medium includes polymers 62 linked to magnetic beads 64. The magnetic beads could be of the type currently available and used for DNA extractions. A magnetic field generated by a suitable magnet 66 could be turned on to pull magnetic beads 64 and the associated polymers 62 to one side of the medium as shown in FIG. 10B. the result is that a region 68 of the medium becomes less viscous. The magnetic particles could be released by switching off the magnetic field to resume the situation illustrated in FIG. 10A wherein the medium in region 68 is more viscous than it is with the magnetic field on.

The magnetic field may be patterned in two dimensions and changed over time such that the viscosity of the medium is a function of both time and position in the medium.

In an alternative embodiment illustrated in FIGS. 10C and 10D, the particles being transported are themselves magnetic. The driving field, may, for example, be an electrical field. A magnetic field could be switched on periodically to drive the particles toward a drag-inducing surface 67. The magnetic field could be switched off to release the particles from surface 67.

In other embodiments, the medium comprises a magnetorheological fluid so that the medium has a viscosity that inherently varies with the applied magnetic field.

Example 14

Acceleration as a Driving Field

A gravitationally induced flow in a density gradient may be used as a driving field. consider, for example, a tube filled with a medium, such as a solution in which heavier or lighter particles are suspended. The tube is located in a centrifuge so that the particles tend to travel toward one end of the tube. The orientation of the tube is periodically reversed. A suitable mobility-varying field could be applied in time with the reversals of orientation so that the particles are caused to achieve net motion in one direction along the tube.

Example 15

SCODA for Desalination

Consider an electrically insulating capillary filled with a saline solution. If the fluid in the capillary is caused to flow then a parabolic velocity profile is established in the capillary. Fluid flows more quickly at the centre of the capillary than near the capillary walls. If an electric field is established across the capillary, ions will build up preferentially within a Debye length (charge screening length) of the capillary walls as required to cancel the applied electric field. This changes the radial distribution of ions in the capillary and thus changes the average velocity of the ions. If the fluid flow is caused to reverse periodically and the electric field is applied only for one direction of flow then there will be a net transport of ions in one direction along the capillary until the SCODA induced drift is counteracted by diffusion from the accumulated ion density gradient along the capillary.

By applying a slight DC bias to the AC fluid flow in a direction opposite to the direction of ion transport, the fluid emerging from the capillary will have a reduced ion content.
Some Possible Variations to SCODA Methods and Apparatus As described in Example 6 above, where the driving field and mobility varying field are not synchronized with one another, the result is that there is a flow of particles back and forth between two locations as the relative phases of the driving and mobility-varying fields vary. This ability to move particles back and forth between two locations at a controllable frequency may be useful in various contexts.

As will be apparent to those skilled in the art in the light of the foregoing disclosure, many alterations and modifications are possible in the practice of this invention without departing from the spirit or scope thereof. For example:

It is not necessary to generate one of the driving and mobility-varying fields. A suitable existing field, which could comprise a field already present for some other purpose or even noise could be used for one of f(t) or g(t). This existing field can be detected and a second field may be applied in time with the detected field so that the mobility of particles is altered in time with a driving field to produce a net drift.

Physically rotating electrodes at constant voltage could be used to simulate the rotating field used for 2D SCODA.

Small DC biases can be used to shift the position of focused spots.

Some embodiments of the invention provide wells in the medium at locations where particles are expected to be concentrated by SCODA. The wells may be filled with a suitable buffer solution. Particles can diffuse into the wells as a result of SCODA induced concentration gradient. Particles can be extracted from the wells with a pipette or other transfer device.

Particle Extraction Methods and Apparatus

Various methods for moving and/or concentrating particles are described above. Often, after particles have been concentrated, it is desirable to remove the particles from the medium in which they have been concentrated. For example, where DNA is concentrated in a gel, it is often desirable to extract the DNA from the gel for subsequent processing.

The following description explains methods and apparatus which may be used to extract particles from a medium. These methods and apparatus may be called "interface zero integrated field electrophoresis" ("IZIFE") methods and apparatus. IZIFE may be used to extract particles that have been moved to a location and/or concentrated by a SCODA method IZIFE also has more general application in extracting particles from media.

IZIFE exploits differences in the mobility properties of particles in different media (such as a gel medium and a buffer medium). Some charged particles (such as molecules of DNA) exhibit an electrophoretic mobility in gel solution (such as agarose gel) that depends on the magnitude of the electric field applied. Such particles can be caused to drift in one direction in such media by applying an electric field that varies asymmetrically with time. However, when those particles are in buffer or free solution, they have an electrophoretic mobility which is constant or at least has a much lower dependence on electric field strength. Therefore, the particles stop drifting if they are carried into a medium where they have a mobility that does not vary with applied field.

Application of ZIFE (zero-integrated-field-electrophoresis) to a gel containing charged particles will cause the particles to drift in the direction that yields the greater mobility. If the particles enter a region containing a buffer or free solution, they will stop drifting. Continued application of a zero time-averaged electric field causes no net drift on the particles in the buffer solution. Therefore, the particles tend to become concentrated in the buffer solution adjacent to the interface between the buffer solution and the gel.

The extraction methods detailed herein permit particles to be extracted from a medium. The invention may be applied to extracting charged biopolymers such as DNA, RNA and polypeptides from electrophoresis media, for example. Some embodiments of the invention use ZIFE to move particles from a medium, such as an electrophoresis gel, into an adjacent fluid. ZIFE is a form of Alternating Current (AC) electrophoresis where, the polarity of an applied electric field reverses periodically and the time-averaged electric field is zero. The intensity of the electric field is greater in one polarity than in the other.

Figure 11:
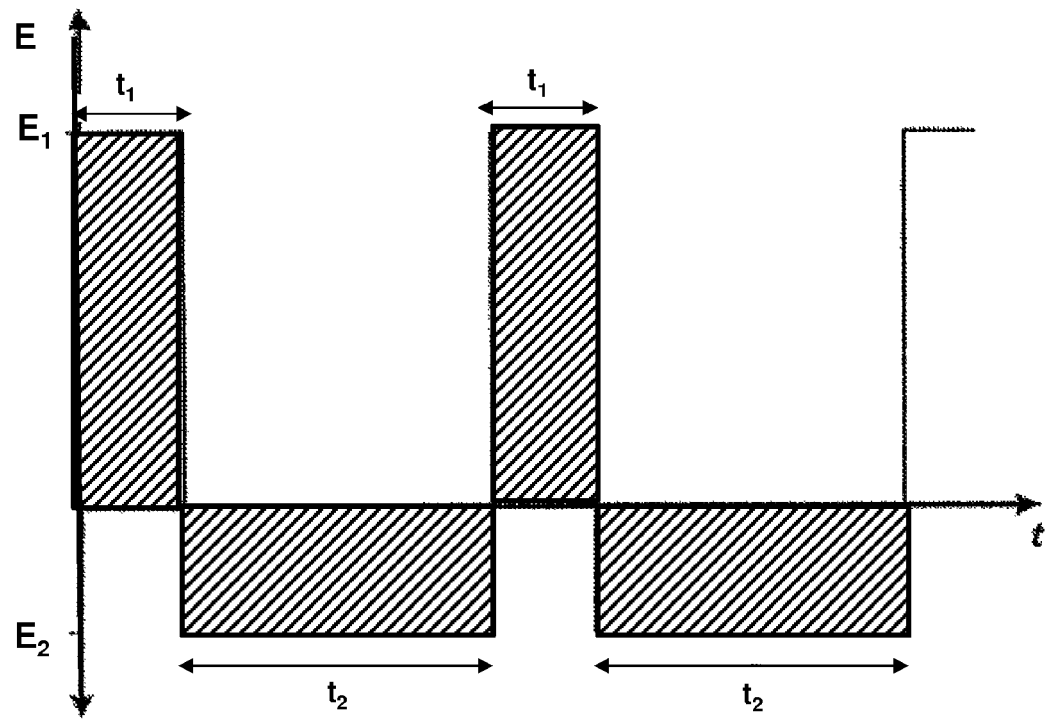
FIG. 11 is a graphical illustration of an exemplary electric field pulse used in ZIFE.

FIG. 11 is a graphical illustration of an exemplary electric field pulse used in ZIFE. As shown in FIG. 11, the pulse comprises an electric field $E_1$ applied in the positive, or "forward", direction for a time $t_1$, followed by an electric field $E_2$ applied in the negative, or "reverse", direction for a time $t_2$. If $E_2=-E_1/r_\epsilon$ (where $r_\epsilon$ is the field ratio), and $t_2=t_1 r_\epsilon$, then the time-averaged electric field is zero. The time-averaged electric field is graphically represented by the shaded areas in FIG. 1. The "positive" shaded areas (corresponding to $E_1$) cancel the "negative" shaded areas (corresponding to $E_2$). Overall there is a zero net electric field. If the time-averaged electric field is exactly zero, then the ZIFE process is unbiased. If the time-averaged electric field deviates from zero, then the ZIFE process is biased The velocity v of a particle moving in a local electric field of amplitude E and having an electrophoretic mobility μ is given by:

$$v=\mu E \quad (27)$$

For linear systems, μ is constant. Particles having constant electrophoretic mobility have no net migration in a medium (i.e. their net velocity is zero) when ZIFE is applied to the medium. By contrast, in non-linear systems, particles have an electrophoretic mobility that is dependent on electric field amplitude. In such non-linear systems, there is a net migration of the particles in the direction that yields the greater mobility. In such a non-linear system, the particle velocity may be given by:

$$v=\mu(E)E \quad (28)$$

Suppose that charged particles in a medium have a field-dependent electrophoretic mobility of the form:

$$\mu(E)=\mu_0+kE \quad (29)$$

It can be seen that the mobility of these particles increases with the amplitude of the electric field E. The distance d traveled by the particles under the influence of a constant electric field E is given by d=vt. If an electric field pulse of the form shown in FIG. 11 is applied, the particles will travel a greater distance during $t_1$ (while the pulse has the greater field amplitude) than the distance traveled during $t_2$. This can be shown by applying Equations (27) and (29) to the distance traveled by the particles. Hence, there is a net drift of particles in the "forward" direction, i.e. the direction in which the electric field of amplitude $E_1$ is applied.

This net drift behavior has been demonstrated by DNA molecules in agarose gels. In such gels, DNA molecules have an electrophoretic mobility of the form given by Equation (28). The field dependence of mobility arises from interactions between the DNA molecules and the gel. Therefore, ZIFE can be applied to DNA in an agarose gel to direct particles made up of DNA in a desired direction.

By contrast, application of ZIFE to DNA molecules in a buffer or free solution does not produce a net migration of DNA. This is because the mobility of DNA molecules in buffer solution is not field dependent. The differences in mobility properties of DNA in two media (e.g. a buffer and a gel) can be exploited to move particles from within one medium into another medium where the particles can be accumulated. This can be done by applying a ZIFE field across an interface between the two media.

Consider, for example, applying a ZIFE field across an interface between a gel in which there are DNA molecules and a buffer solution. Applying ZIFE to the molecules of DNA in the gel causes the molecules to migrate in the gel toward the gel-buffer interface. Once those molecules enter the buffer, the molecules will stop migrating. The ZIFE field may have a small bias in the direction which tends to move the molecules from the buffer toward the gel. This bias tends to prevent the molecules from diffusing too far away from the interface after they enter the buffer. The bias may prevent the molecules from encountering the electrode used to create the ZIFE field. The bias is small enough that the particles in the gel continue to move toward the interface (i.e. the ZIFE velocity is not overcome by the net drift resulting from the bias).

Figure 12A:
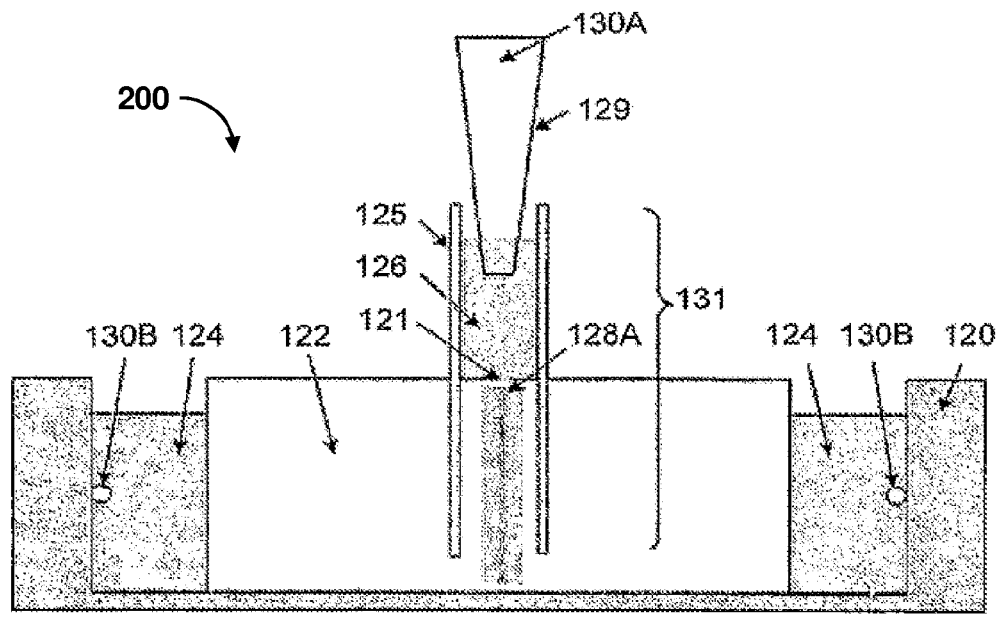
FIG. 12A is a cross-sectional elevation view of an extraction apparatus in accordance with a particular embodiment of the present invention, illustrating molecules of DNA in a solution prior to extraction.
Figure 12B:
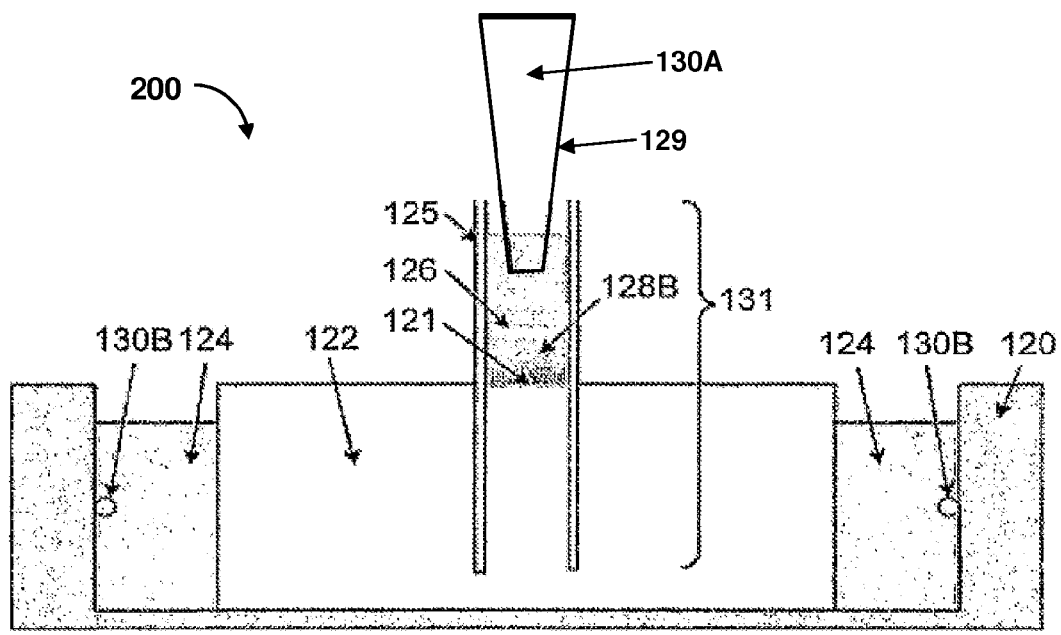
FIG. 12B is a cross-sectional elevation view of the apparatus of FIG. 12A, illustrating molecules of DNA extracted from a solution and concentrated in a small amount of buffer.
Figure 12C:
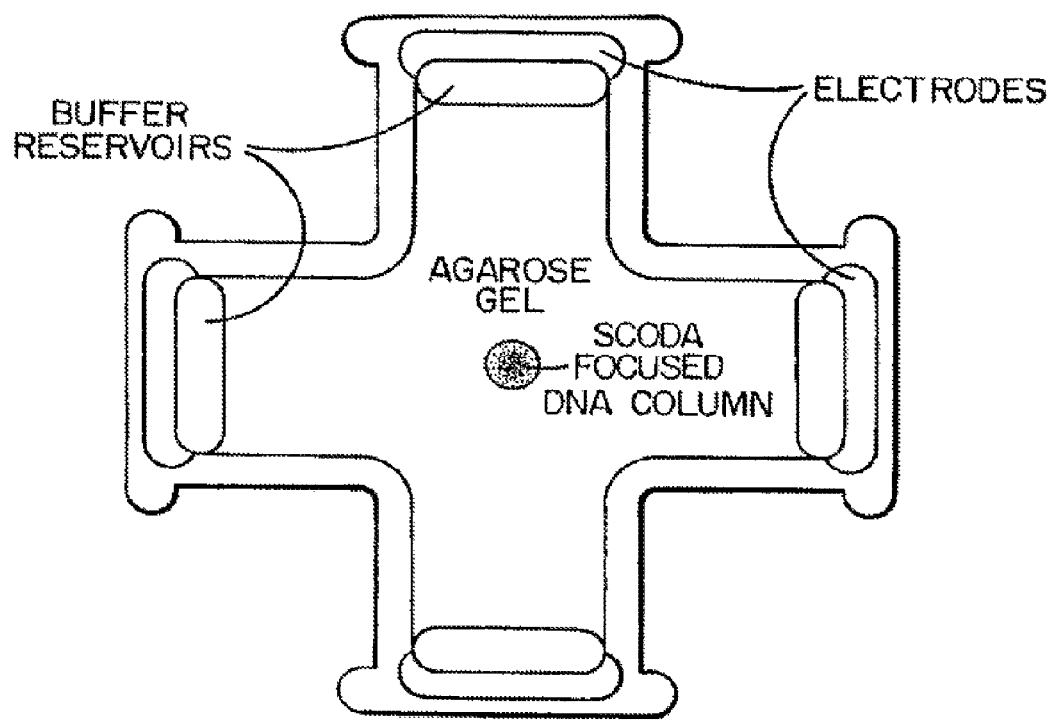
FIG. 12C is a plan view of an extraction apparatus similar to that shown in FIG. 12A.

Apparatus according to one embodiment of the invention is shown in FIGS. 12A and 12B. FIG. 12A shows molecules of DNA in a gel, prior to extraction, and FIG. 12B shows molecules of DNA concentrated in a buffer, after extraction from the gel. An extraction apparatus 200 comprises a gel boat 120 (which may be shaped as a rectangular box) containing a gel 122, such as agarose gel. Gel 122 fills a substantial volume of gel boat 120. Preferably gel 122 is separated from each of electrodes 130B by a buffer solution in a reservoir 124. Reservoirs 124 are separated from one another so that the buffer does not provide short circuit paths between electrodes 130B.

As shown in FIG. 12A, prior to extraction, molecules of DNA 128A are concentrated in a column in gel 122. Molecules 128A are typically not concentrated in such form when left in their natural state. Prior to being concentrated, molecules 128A are typically distributed throughout gel 122. Molecules 128A may be concentrated into a column as shown in FIG. 12A through the use of SCODA, as described above. In the alternative, molecules 128A may be concentrated by another method. For example, the molecules to be extracted may be the molecules of a band of DNA separated by conventional DC electrophoresis or PFGE Concentration of molecules 128A in a region of gel 122 is not required prior to extraction. However, concentration is preferable to facilitate more efficient extraction of the molecules.

A capillary 125 containing a small amount of buffer solution is inserted into gel 122 so as to surround the molecules 128A to be extracted. Capillary 125 may be inserted by a robotic device which permits the location of insertion to be carefully controlled and which inserts the capillary with minimal disturbance of the gel. The robotic device may comprise a multi-axis positioner, such as an X-Y positioner, that positions capillary 125 over a desired location in a medium and then longitudinally extends the capillary into the medium. After capillary 125 is inserted into gel 122, the top portion of capillary 125 contains buffer solution, while the bottom portion of capillary 125 contains gel 122. The buffer solution in capillary 125 provides an extraction reservoir 126 adjacent to gel 122. Extraction reservoir 126 meets gel 122 at a buffer-gel boundary 121. The arrangement of buffer and gel in capillary 125 forms a buffer-gel interface 131. A pipette 129 is provided above capillary 125 to suction molecules 128A after they have migrated into extraction reservoir 126.

To provide the electric fields required for electrophoresis, an electrode 130A is located near the tip of pipette 129. Electrode 130A is preferably located sufficiently far from the interface that the extracted molecules do not encounter electrode 130A while the ZIFE field is being applied. A plurality of electrodes 130B are located in buffer reservoir 124. The electrodes may be made of platinum, for example. More electrodes may be provided than those shown in FIGS. 12A and 12B.

The tip of pipette 129 is filled with a small amount of buffer so as to provide conductivity between electrodes 130A and 130B when the pipette is inserted in capillary 125. In one embodiment, electrodes 130B are ganged to a fixed common potential (for example, electrodes 130B may be grounded), while electrode 130A is set to a different potential. A varying electric field can be applied across buffer-gel interface 131 by varying the potential of electrode 130A.

To perform Interface-ZIFE, a zero time-averaged pulsed electric field is applied across buffer-gel interface 131. The pulsed electric field may be of the form shown in FIG. 1, for example. To cause molecules 128A to migrate in the desired direction (i.e. toward extraction reservoir 126), an electric field having an amplitude $E_1$ is applied in the direction toward extraction reservoir 126, while an electric field having an amplitude $E_2$ is applied in the opposite direction. $E_1$ and $E_2$ are chosen such that the particles to be extracted have a greater mobility under the influence of $E_1$ than they do under the influence of $E_2$. For typical molecules and media $E_1 > E_2$. The polarity is selected so that the particles are driven toward interface 131 under the influence of $E_1$.

Application of Interface-ZIFE across buffer-gel interface 131 will cause molecules 128A in gel 122 to drift toward extraction reservoir 126. After some time, some of the molecules 128A will cross buffer-gel boundary 121 and enter into the buffer in extraction reservoir 126. Once these molecules reach extraction reservoir 126, Interface-ZIFE has no net drift effect on the molecules and the molecules thus stop drifting. Eventually all (or most) of molecules 128A will cross the buffer-gel boundary 121 and migrate into extraction reservoir 126. Molecules 128A become concentrated in the buffer adjacent the interface.

FIG. 12B shows molecules 128B (corresponding to molecules 128A in FIG. 2a) that have migrated from gel 122 into extraction reservoir 126. Thus, Interface-ZIFE can be used to collect and concentrate molecules 128B in extraction reservoir 126. Pipette 129 or another device can then suction molecules 128B from extraction reservoir 126, thereby completing the extraction process.

Figure 13:
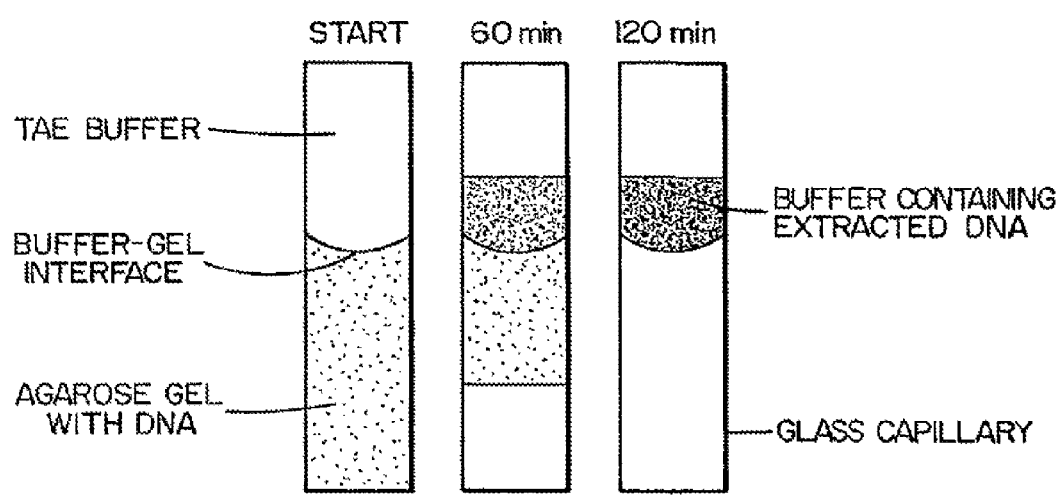
FIG. 13 shows a glass capillary in an extraction experiment using the apparatus and method in accordance with a particular embodiment of the invention.

FIG. 13 shows a glass capillary in an extraction experiment in which DNA mixed with a liquid gel was allowed to set within a capillary tube. Buffer was added to an upper portion of the capillary. The techniques described above were used to extract the DNA. An image of the capillary was captured at various times (0 minutes, 60 minutes, 120 minutes) to show the effects of Interface-ZIFE applied to a buffer-gel interface. The buffer is a TAE (Tris-Acetate-EDTA) buffer and the gel is an agarose gel containing DNA. To perform this experiment, 100 µL of liquid 1% agarose gel, mixed with 5 µL λ DNA and 2.5 µg EtBr, was pipetted into the lower portion of a 2.5 mm inner diameter glass capillary and allowed to solidify. The upper portion of the capillary was filled with approximately 50 µL of 0.1×TAE buffer and a first platinum electrode was inserted into the buffer. The bottom of the capillary was then submerged in a shallow reservoir of 0.1×TAE buffer with a second platinum electrode.

Interface-ZIFE was performed with these conditions: periodically, a voltage $V_1 = 200$ V was applied to the first electrode for a time $t_1 = 8$ s, then a voltage $V_2 = -100$ V was applied to the second electrode for $t_2 = 16$ s. The electric field was pulsed for 2 hours. The electrodes were separated by 5 cm. Over the course of the experiment, the upper half of the capillary remained filled with buffer and the DNA remained in a relatively small volume (approximately 20 µL). As shown by the images of the capillary, there is a progressive migration of DNA through a gel and concentration of the DNA in a small amount of buffer above the gel.

If extraction reservoir 126 is sufficiently small, then molecules 128B that are concentrated in a region in extraction reservoir 126 will leave their concentrated region only by diffusion, which is slow over long distances. Convective mixing of molecules 128B and extraction buffer 126 should be minimized to maintain molecules 128B in their concentrated region. To minimize convective mixing, capillary 125 should preferably have a small diameter. Moreover, extraction buffer 126 and gel 122 are preferably kept at the same temperature.

In one embodiment, pipette 129 comprises a mechanized pipettor with built-in electrode 130A. The mechanized pipettor aspirates buffer into a disposable pipette tip, then partially dispenses the buffer to cover the gel inside capillary 125 so that there is conductivity between electrodes 130A and 130B. Computer monitoring may be used to monitor the current between electrodes 130A and 130B during extraction, and detect such problems as bubbles or evaporation that may create an open circuit between the electrodes. After extraction is complete, the remaining buffer in the pipette tip is disposed of, and the pipette tip may return to capillary 25 to extract further samples of particles. Mechanized pipetting may reduce unnecessary pipette tip motion so that there is minimal mixing of the concentrated particles with the surrounding buffer. This minimizes the extraction volume and hence increases final concentration of the particles to be extracted.

In another embodiment, instead of inserting a capillary filled with buffer into the gel, the gel may be cast with a cavity. The cavity is filled with a buffer solution, and a pipette having an electrode is inserted into the buffer. The cavity functions similarly to the capillary in collecting the particles for extraction. Molecules may be caused to enter such a cavity from the surrounding medium by generating a concentration gradient between the medium and the cavity by SCODA.

Figure 14:
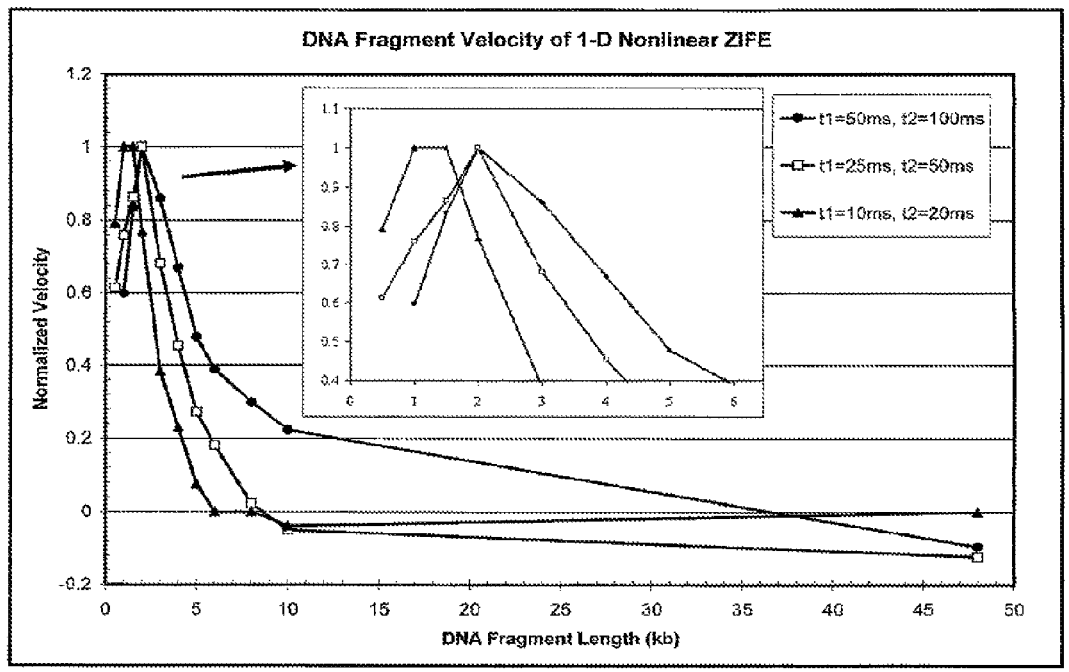
FIG. 14 is a graph illustrating the DNA fragment velocity during an experiment as a function of fragment length and cycle times; and, FIG. 15 shows a comparison between a DNA fragment mix and the fragment distribution of the same mix, after extraction.

Interface-ZIFE extraction of DNA mixtures from gels may be applied to selectively extract DNA fragments according to their size. If cycle times $t_1$ and $t_2$ for the electric field pulse are chosen to be sufficiently small, the relaxation or re-orientation time of the DNA molecules becomes significant and introduces a length-dependence in the migration velocity of the molecules. FIG. 14 is a graph illustrating the DNA fragment velocity during an experiment as a function of fragment length and cycle times $t_1$ and $t_2$. In that experiment, DNA fragments of different lengths were linearly separated using standard DC electrophoresis in a 1% agarose gel (0.1×TAE). ZIFE was then applied (in a direction perpendicular to that in which the DC electrophoresis was performed) to observe non-linear velocity of the fragments.

Figure 15:
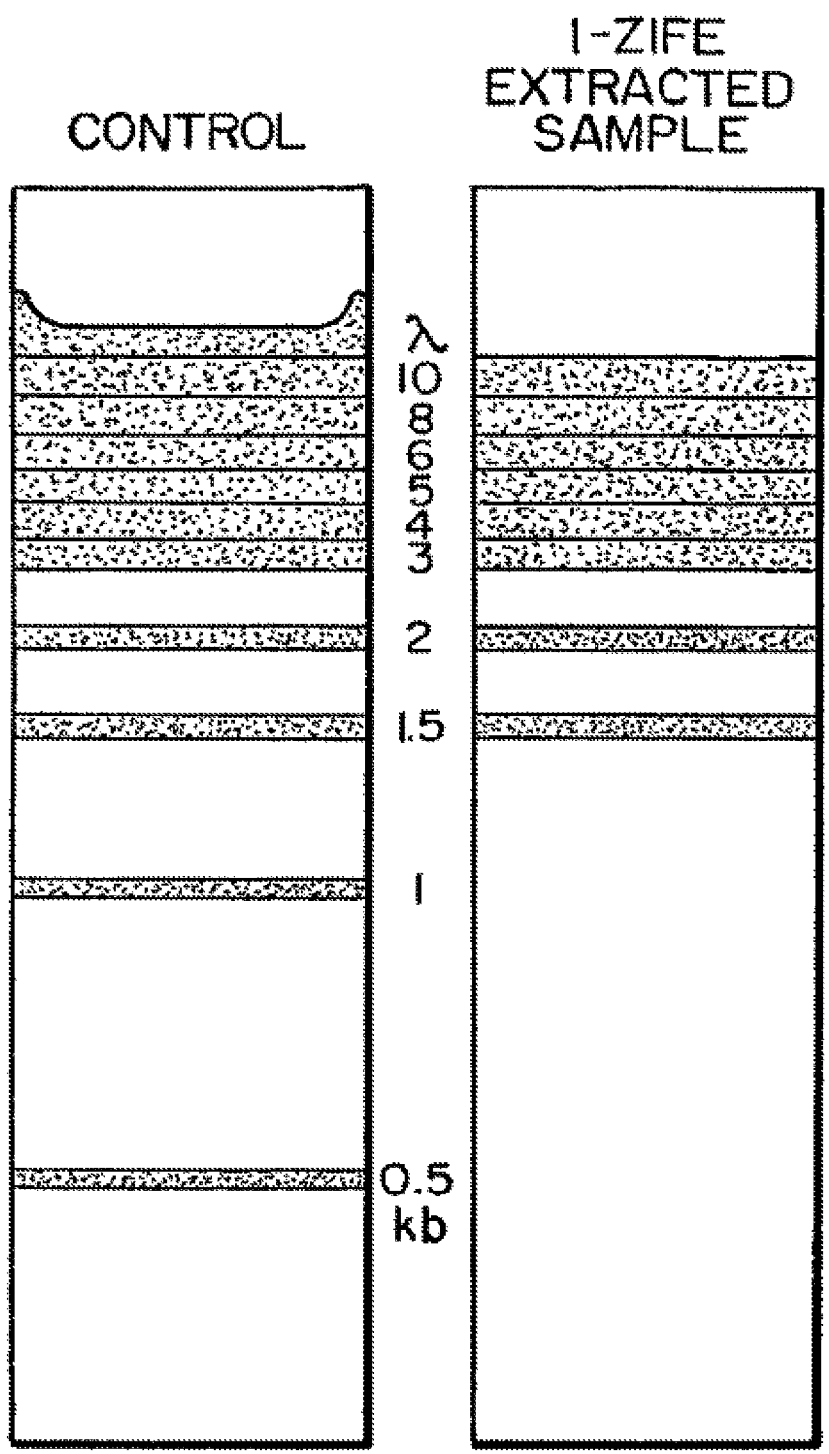

FIG. 15 shows a comparison between a DNA fragment mix and the fragment distribution of the same mix, after Interface-ZIFE extraction. The mix comprised 2 µL λ DNA (48 kb, 500 ng/µL) and 4 µL 1 kb DNA ladder (0.5-10 kb, 500 ng/µL) and was run in 100 µL of 1% agarose gel applying the Interface-ZIFE extraction method described above. A pulsed electric field was applied, generated by a voltage $V_1 = 200$V applied to the electrode in the pipette for a time of $t_1 = 25$ ms, which alternated with a voltage $V_2 = -100$V applied to the electrodes in the gel for a time of $t_2 = 50$ ms. The pulsed electric field was applied for 3 hours. This process extracted DNA into 0.1×TAE buffer which was mixed with loading dye and inserted into the well of a 1% agarose gel, along with a control from the original mix, for standard DC electrophoresis. The λ DNA band and short (less than 1 kb) fragments were not extracted from the gel. The size selection of Interface-ZIFE may be applied to longer fragments (100-200 kb) *as well*.

Parameters that can be varied to optimize extraction speed, extraction efficiency and DNA fragment length selectivity, include: magnitude of the electric pulsed field; frequency (cycle times) of the electric pulsed field; composition of the buffer in extraction reservoir 126; composition of gel 122; operating temperature; and the degree of concentration of molecules 128A.

The methods and apparatus disclosed herein may be applied for extracting charged particles from a medium where the particles are concentrated in a particular region of the medium (such as DNA molecules concentrated in a column or pillar in gel). However, the methods and apparatus are not limited to such application. They may also be employed to extract charged particles that are uniformly dispersed in the medium, located or concentrated in particular regions or bands, or otherwise distributed in the medium. Using the methods and apparatus disclosed herein, charged particles, and in particular biopolymers (for example, DNA, RNA and polypeptides), may be extracted from acrylamide, linear poly-acrylamide, POP (Perkin Elmer), agarose gels, entangled liquid solutions of polymers, viscous or dense solutions, solutions of polymers designed to bind specifically to the molecules whose motion is being directed, simple aqueous solutions, and the like. Interface-ZIFE used in conjunction with SCODA-based electrophoresis (for concentrating the DNA in a region) can be used to extract bacterial artificial chromosomes, plasmids and high molecular weight or genomic DNA.

IZIFE can be used to extract only selected particles from a medium. Particles having velocities that depend only linearly on the magnitude of an applied driving field will simply oscillate back and forth when exposed to an IZIFE driving field. Such particles will therefore remain in the medium while other particles having velocities having a non-linear dependence on applied field can be extracted from the medium. In some cases the IZIFE driving field can be constructed so that different particle species drift toward the second medium at different rates. The concentration of the different species at the interface between the media will therefore vary over time. A species which has a high net drift velocity under IZIFE will be extracted from the first medium before a species which has a lower net drift velocity.

By terminating IZIFE before slower species have been extracted from the first medium, the relative concentration of species having faster net drift velocities can be increased. By removing faster species that have accumulated at the interface before slower drifting species have arrived at the interface, one can increase the relative concentration at the interface of species having slower net drift velocities under IZIFE Some Possible Variant Particle Extraction Methods and Apparatus As will be apparent to those skilled in the art in the light of the foregoing disclosure, many alterations and modifications are possible in the practice of this invention without departing from the spirit or scope thereof, including but not limited to the following:

The extraction of uncharged, or electrically neutral, molecules may be accomplished using the methods and apparatus disclosed herein if those molecules are carried by charged molecules. For example, neutral proteins that interact with charged micelles may be extracted electrophoretically through their interaction with the micelles.

The waveform used for implementing ZIFE may be biased in one direction or the other. Biased ZIFE may facilitate selective separation of the particles according to their size.

Instead of using IZIFE to extract particles from a first medium into a second medium, one could use SCODA to extract particles from the first medium into a second medium. In some such embodiments a SCODA driving field that alternates in direction is directed across an interface between the first and second media. The SCODA driving field may, for example, be directed substantially perpendicularly to the interface. A SCODA mobility-varying field may be selected such that the mobility-varying field affects the mobility of the particles in the first medium so as to cause the particles in the first medium to travel in a direction toward the second medium. The mobility-varying field is selected to affect the mobility of the particles the second medium to a degree substantially less than it affects the mobility of the particles in the first medium. In the best case the mobility-varying field does not affect the mobility of particles in the second medium. In this example, the SCODA effect causes particles to be transported from the first medium into the second medium where the particles become concentrated at the interface between the first and second media. In an alternative embodiment, the mobility-varying field is applied only to those particles that are within the first medium so that the particles drift by SCODA into the second medium and become concentrated in the second medium.

Where a component (e.g. a power supply, electrode, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Accordingly, the scope of the invention is to be construed in accordance with the substance defined by the following claims.

The invention claimed is:

1. A method for causing motion of target nucleic acids in contact with a separation medium, the method comprising:
    applying a first time-varying driving field to the target nucleic acids with a first electrode adjacent the separation medium;
    applying a second time-varying driving field to the target nucleic acids with a second electrode adjacent the separation medium;
    applying a third time-varying driving field to the target nucleic acids with a third electrode adjacent the separation medium; and
    synchronously varying the mobility of the target nucleic acids in the medium, wherein the first, second, and third electrodes are adjacent a perimeter of the separation medium and approximately equidistant from each other.

2. The method of claim 1, wherein the mobility of the target nucleic acids is varied by changing a temperature of the separation medium.

3. The method of claim 2, wherein the temperature is varied with Joule heating.

4. The method of claim 1, wherein the separation medium comprises a polymer.

5. The method of claim 1, wherein the separation medium comprises bound oligonucleotides.

6. The method of claim 5, wherein the bound oligonucleotides are complimentary to a portion of the target nucleic acids.

7. The method of claim 1, wherein the target nucleic acids comprise 200 or fewer nucleotides.

8. A method of separating a target nucleic acid from a sample comprising other nucleic acids, comprising:
    loading a sample comprising a target nucleic acid and other nucleic acids on a separation medium; and
    applying a time-varying driving field to the medium while synchronously varying the mobility of the nucleic acids in the separation medium, thereby separating the target nucleic acid from the other nucleic acids by causing the target nucleic acid to bind and unbind to the medium at a sequence-specific rate or a sequence-specific strength that is different from the rate or strength of the other nucleic acids having different sequences.

9. The method of claim 8, wherein the mobility of the nucleic acids in the separation medium is varied by changing a temperature of the separation medium.

10. The method of claim 9, wherein the temperature is varied with Joule heating.

11. The method of claim 8, wherein the separation medium comprises a polymer.

12. The method of claim 8, wherein the separation medium comprises bound oligonucleotides.

13. The method of claim 8, wherein the target nucleic acid comprises 200 or fewer nucleotides.

\* \* \* \* \*